United States Patent
Bey et al.

(10) Patent No.: US 10,058,601 B2
(45) Date of Patent: *Aug. 28, 2018

(54) **ATTENUATED *MANNHEIMIA HAEMOLYTICA* VACCINES AND METHODS OF MAKING AND USE**

(71) Applicant: MERIAL, INC., Duluth, GA (US)

(72) Inventors: Russell F. Bey, Arden Hills, MN (US); Paulraj Kirubakaran Lawrence, Worthington, MN (US); Randy R. Simonson, Worthington, MN (US)

(73) Assignee: MERIAL INC., Duluth, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/594,451

(22) Filed: May 12, 2017

(65) Prior Publication Data

US 2017/0246286 A1 Aug. 31, 2017

Related U.S. Application Data

(60) Continuation of application No. 14/991,003, filed on Jan. 8, 2016, now Pat. No. 9,675,682, which is a division of application No. 14/075,169, filed on Nov. 8, 2013, now Pat. No. 9,370,561.

(60) Provisional application No. 61/723,979, filed on Nov. 8, 2012.

(51) Int. Cl.
| | |
|---|---|
| *A61K 39/02* | (2006.01) |
| *A61K 49/00* | (2006.01) |
| *A61K 39/00* | (2006.01) |
| *A61K 39/102* | (2006.01) |
| *C07K 14/285* | (2006.01) |
| *C12N 1/36* | (2006.01) |

(52) U.S. Cl.
CPC .......... *A61K 39/102* (2013.01); *C07K 14/285* (2013.01); *C12N 1/36* (2013.01); *A61K 2039/522* (2013.01); *A61K 2039/543* (2013.01); *A61K 2039/552* (2013.01); *A61K 2039/70* (2013.01)

(58) Field of Classification Search
CPC ...... A61K 39/102; A61K 45/00; A61K 47/00; C12R 1/00; C12N 15/00
USPC ......... 424/9.1, 9.2, 93.2, 93.3, 184.1, 190.1, 424/234.1, 255.1, 278.1; 435/41, 69.1, 435/440
See application file for complete search history.

(56) References Cited

U.S. PATENT DOCUMENTS

| | | | |
|---|---|---|---|
| 5,055,400 A | 10/1991 | Lo et al. | |
| 5,476,657 A | 12/1995 | Potter | |
| 5,587,305 A | 12/1996 | Briggs et al. | |
| 5,733,780 A | 3/1998 | Briggs et al. | |
| 5,824,525 A | 10/1998 | Briggs et al. | |
| 5,824,556 A | 10/1998 | Tarr | |
| 5,849,305 A | 12/1998 | Briggs et al. | |
| 5,871,750 A | 2/1999 | Potter | |
| 6,180,112 B1 | 1/2001 | Highlander et al. | |
| 6,331,303 B1 | 12/2001 | Briggs et al. | |
| 6,495,145 B2 | 12/2002 | Briggs et al. | |
| RE38,028 E | 3/2003 | Briggs et al. | |
| 6,573,093 B2 | 6/2003 | Briggs et al. | |
| 6,610,307 B1 | 8/2003 | Prideaux et al. | |
| 6,793,927 B1 | 9/2004 | Briggs et al. | |
| 6,936,262 B2 | 8/2005 | Briggs et al. | |
| 7,351,416 B2 | 4/2008 | Briggs et al. | |
| 9,370,561 B2 * | 6/2016 | Bey .................. | A61K 39/102 |
| 9,675,682 B2 * | 6/2017 | Bey .................. | A61K 39/102 |
| 2002/0039589 A1 | 4/2002 | Briggs et al. | |
| 2011/0296545 A1 | 12/2011 | Srikumaran et al. | |
| 2014/0170190 A1 | 6/2014 | Bey et al. | |
| 2016/0158336 A1 | 6/2016 | Bey et al. | |
| 2016/0243212 A1 | 8/2016 | Briggs et al. | |
| 2017/0022510 A1 | 1/2017 | Briggs et al. | |
| 2017/0128560 A1 | 5/2017 | Briggs et al. | |

OTHER PUBLICATIONS

Briggs et al. Generation of Molecular Characterization of New Temperature-Sensitive Plasmids Intended for Genetic Engineering of *Pasteurellaceae*.

Briggs et al. Mucosal and parenteral vaccination against pneumonic pasteurellosis in cattle with a modified-live in-frame lktA deletion mutant of *Mannheimia haemolytica*. Microbial Pathogenesis 52 (2012) 302-309.

Cortese VS et al. Serologic response to Mannheimia haemolytica in calves concurrently inoculated with inactivated or modified-live preparations of M haemolytica and viral combination vaccines containing modified-live bovine herpesvirus type 1. AJVR, vol. 72, No. 11, Nov. 2011. 1541.

Crouch CF et al. Cross protection of a *Mannheimia haemolytica* A1 lkt- / *Pasteurella multocida* ΔhyaE bovine respiratory disease vaccine against experimental challenge with *Mannheimia haemolytica* A6 in calves. Vaccine 30 (2012) 2320-2328.

(Continued)

*Primary Examiner* — Rodney P Swartz

(74) *Attorney, Agent, or Firm* — Judy Jarecki-Black; Richard Seeger; Merial Inc.

(57) ABSTRACT

The present invention provides attenuated *M. haemolitica* strains that elicit an immune response in animal against *M. haemolitica*, compositions comprising said strains, methods of vaccination against *M. haemolitica*, and kits for use with such methods and compositions. The invention further provides multi-valent vaccines, which provide protective immunity when administered in an effective amount to animals susceptible to "shipping fever" or bovine respiratory disease.

19 Claims, 5 Drawing Sheets

Figure 1A:
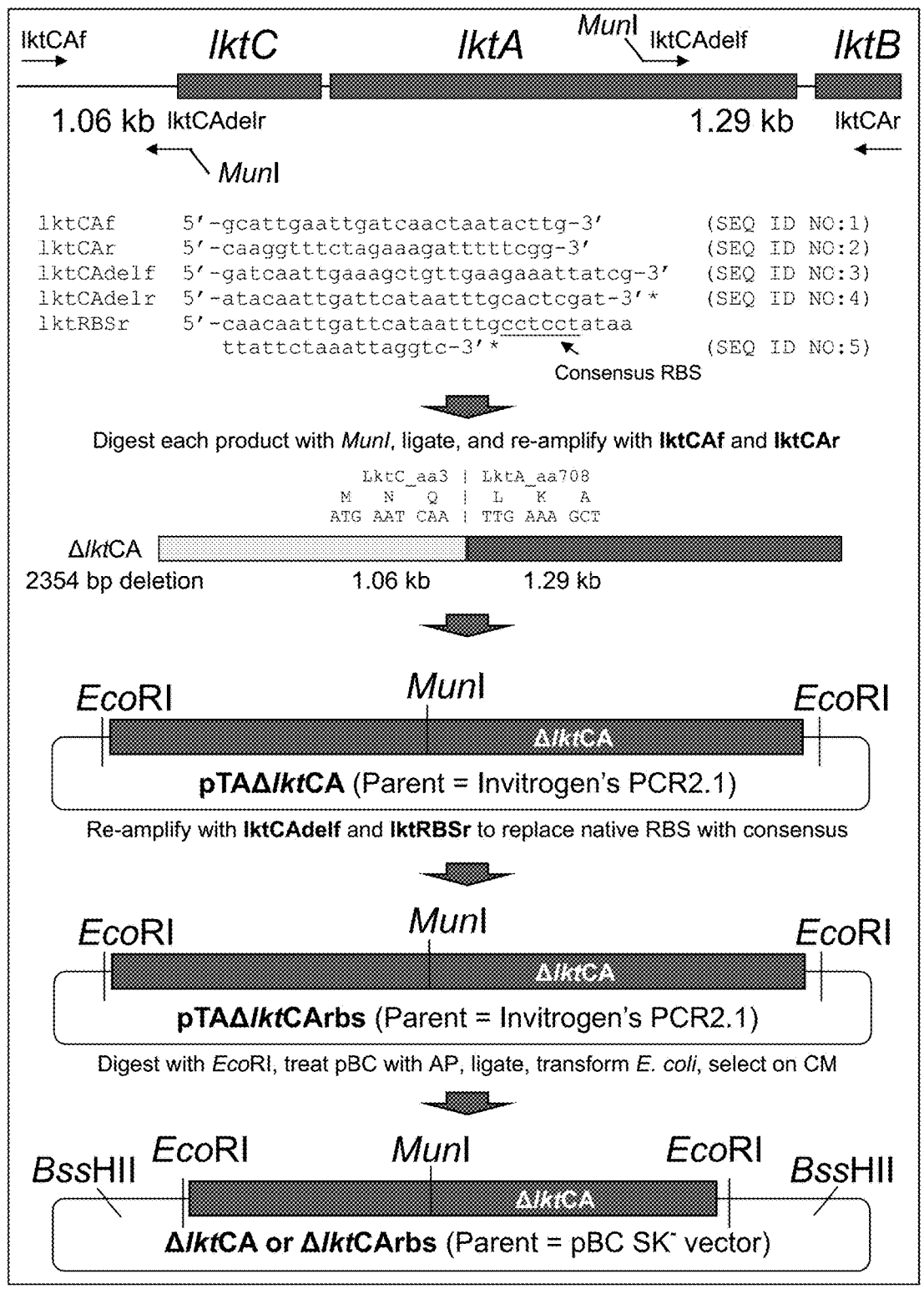

Specification includes a Sequence Listing.

(56) References Cited

OTHER PUBLICATIONS

Frank GH et al. Effect of intranasal exposure to leukotoxin-deficient *Mannheimia haemolytica* at the time of arrival at the feedyard on subsequent isolation of *M haemolytica* from nasal secretions of calves. AJVR, vol. 64, No. 5, May 2003. 580.

Jeyaseelan S et al. *Mannheimia haemolytica* Leukotoxin Activates a Nonreceptor Tyrosine Kinase Signaling Cascade in Bovine Leukocytes, which Induces Biological Effects. Infection and Immunity, vol. 69, No. 10. Oct. 2001, p. 6131-6139.

* cited by examiner

SEQUENCE LISTING

<160> NUMBER OF SEQ ID NOS: 26

<210> SEQ ID NO 1
<211> LENGTH: 26
<212> TYPE: DNA
<213> ORGANISM: Artificial Sequence
<220> FEATURE:
<223> OTHER INFORMATION: lktCAf primer

<400> SEQUENCE: 1
gcattgaatt gatcaactaa tacttg                                         26

<210> SEQ ID NO 2
<211> LENGTH: 25
<212> TYPE: DNA
<213> ORGANISM: Artificial Sequence
<220> FEATURE:
<223> OTHER INFORMATION: lktCAr primer

<400> SEQUENCE: 2
caaggtttct agaaagattt ttcgg                                          25

<210> SEQ ID NO 3
<211> LENGTH: 31
<212> TYPE: DNA
<213> ORGANISM: Artificial Sequence
<220> FEATURE:
<223> OTHER INFORMATION: lktCAdelf primer

<400> SEQUENCE: 3
gatcaattga aagctgttga agaaattatc g                                   31

<210> SEQ ID NO 4
<211> LENGTH: 29
<212> TYPE: DNA
<213> ORGANISM: Artificial Sequence
<220> FEATURE:
<223> OTHER INFORMATION: lktCAdelr primer

<400> SEQUENCE: 4
atacaattga ttcataattt gcactcgat                                      29

<210> SEQ ID NO 5
<211> LENGTH: 48
<212> TYPE: DNA
<213> ORGANISM: Artificial Sequence
<220> FEATURE:
<223> OTHER INFORMATION: lktRBSr primer

<400> SEQUENCE: 5
caacaattga ttcataattt gcctcctata attattctaa attaggtc                 48

<210> SEQ ID NO 6
<211> LENGTH: 1068
<212> TYPE: DNA
<213> ORGANISM: Artificial Sequence
<220> FEATURE:
<223> OTHER INFORMATION: 5' deltalktCA PCR fragment

<400> SEQUENCE: 6
gcattgaatt gatcaactaa tacttggttt ttcaagtgag ttgcaatgcc taaaccatca      60
ccaaaatagt ttggattatt gatttctcc cctacaaaat ctagcccttc gtgttttctt     120
gccatctcag ccaataccgg cacatcgcca aaaatagcat caattcgccc attttgcaca    180
tctaaaatag cattttgata agaggcataa gatttcacat tgtactcttt tttctctttt    240

```
gctaaatagt gttggtaagt agtcccattt tgcacaccaa tcgttttcac cttagcaaaa      300
tctgtatctt ttttcgcaat gaaggcagca gagcttggaa agtaaggctc gctaaataat      360
acttgtttct tacgtggttc cgtaataccc atacctgaaa ttgcagcatc aaattgtttt      420
tgttttaggc tttggattaa gctatcaaaa ggttggctat ggaatgtaca atttgcattc      480
atctctttac agatagcatt tgcaatatcc acatcaaaac cgataatttc tcccttctct      540
tcggtcattt caaatggagg atagcttggc tccatcacaa atttgatatc ttgtgcctgc      600
gcagtaacca cacccgaa taaagggtc aaagtgttt ttcataaa agtccctgt             660 gttttcatta taaggattac cactttaacg cagttacttt cttaaaaaaa gtcttctttt      720
cataaagttt gttttatgtc atacaaacac atcaaattga gatgtagttt ctcaatcctc      780
ttgattcctc tatctcaaaa aaacaaccca aagaaaaaa gaaagtata tgttacatta        840 atattacaat gtaattattt tgtttaattt ccctacattt tgtataactt taaaacactc      900 cttttctct tctgattata taaaagacaa aaaataacaat ttaagctaca aaaaacaaca      960
aaaaacaaca aaaaacacga caataagatc gagtaatgat tatattatgt tataattttt     1020
gacctaattt agaataatta tcgagtccaa attatgaatc aattgtat                  1068
```

<210> SEQ ID NO 7
<211> LENGTH: 1295
<212> TYPE: DNA
<213> ORGANISM: Artificial Sequence
<220> FEATURE:
<223> OTHER INFORMATION: 3' deltalktCA PCR fragment

<400> SEQUENCE: 7

```
caattgaaag ctgttgaaga aattatcggt acatcacata acgatatctt taaaggtagt       60
aagttcaatg atgcctttaa cggtggtgat ggtgtcgata ctattgacgg taacgacggc      120
aatgaccgct tatttggtgg taaaggcgat gatattctcg atggtggaaa tggtgatgat      180
tttatcgatg gcggtaaagg caacgaccta ttacacggtg gcaagggcga tgatattttc      240
gttcaccgta aaggcgatgg taatgatatt attaccgatt ctgacggcaa tgataaatta      300
tcattctctg attcgaactt aaaagattta acatttgaaa aagttaaaca taatcttgtc      360
atcacgaata gcaaaaaaga gaaagtgacc attcaaaaact ggttccgaga ggctgatttt      420
gctaaagaag tgcctaatta taaagcaact aaagatgaga aaatcgaaga aatcatcggt      480
caaaatggcg agcggatcac ctcaaagcaa gttgatgatc ttatcgcaaa aggtaacggc      540
aaaattaccc aagatgagct atcaaaagtt gttgataact atgaattgct caaacatagc      600
aaaaatgtga caaacagctt agataagtta atctcatctg taagtgcatt tacctcgtct      660
aatgattcga gaaatgtatt agtggctcca acttcaatgt tggatcaaag tttatcttct      720
cttcaatttg ctagagcagc ttaatttta atgattggca actctatatt gtttcacaca      780
ttatagagtt gccgttttat tttataaaag gagacaatat ggaagctaac catcaaagga      840
atgatcttgg tttagttgcc ctcactatgt tggcacaata ccataatatt tcgcttaatc      900
cggaagaaat aaaacataaa tttgatcttg acggaaaagg gctttcttta actgcttggc      960
ttttagctgc aaaatcgtta gcgttgaaag cgaaacacat taaaaagag atttcccgct     1020 tacacttggt gaatttaccg gcattagttt ggcaagataa cggtaaacat ttttttattgg    1080 taaaagtgga taccgataat aaccgctatt taacttacaa tttggaacaa gatgctccac    1140
aaattctgtc acaagacgaa tttgaagcct gctatcaagg gcagttaatt ttggtcacgt    1200
```

```
ccagagcttc cgtagtaggt caattagcaa agttcgattt cacctggttt attccggcgg    1260
tgatcaaata ccgaaaaatc tttctagaaa ccttg                               1295
```

<210> SEQ ID NO 8
<211> LENGTH: 27
<212> TYPE: DNA
<213> ORGANISM: Artificial Sequence
<220> FEATURE:
<223> OTHER INFORMATION: BCCT FAMILY-BETAINE-CARNITINE-CHOLINE
      Transporter forward primer

<400> SEQUENCE: 8

```
atgttattcg ccgccggaat ggggatc                                         27
```

<210> SEQ ID NO 9
<211> LENGTH: 25
<212> TYPE: DNA
<213> ORGANISM: Artificial Sequence
<220> FEATURE:
<223> OTHER INFORMATION: BCCT FAMILY-BETAINE-CARNITINE-CHOLINE
      Transporter reverse primer

<400> SEQUENCE: 9

```
acctgcatca ccccaaagcc aagtg                                           25
```

<210> SEQ ID NO 10
<211> LENGTH: 26
<212> TYPE: DNA
<213> ORGANISM: Artificial Sequence
<220> FEATURE:
<223> OTHER INFORMATION: IGA SPECIFIC SERINE METALLO-ENDOPEPTIDASE
      forward primer

<400> SEQUENCE: 10

```
atgaagacca aaacatttac tcgttc                                          26
```

<210> SEQ ID NO 11
<211> LENGTH: 25
<212> TYPE: DNA
<213> ORGANISM: Artificial Sequence
<220> FEATURE:
<223> OTHER INFORMATION: IGA SPECIFIC SERINE METALLO-ENDOPEPTIDASE
      reverse primer

<400> SEQUENCE: 11

```
agcgcttgtg tccctgaacc agcac                                           25
```

<210> SEQ ID NO 12
<211> LENGTH: 2007
<212> TYPE: DNA
<213> ORGANISM: Artificial Sequence
<220> FEATURE:
<223> OTHER INFORMATION: A6 specific gene-BCCT FAMILY/BETAINE/
      CARNITINE/CHOLINE transporter

<400> SEQUENCE: 12

```
ttggatttaa tcaaaaaatt aaacacagga agtacccttta gggtaccgat tttcctaccg    60
agtttactct tgtcagcttt tgttgccgtt tctgtatca tctttccaca gcaagcacaa     120
acctcacttg ataccatcaa aaatagtctc ttccaacatt ttagctggtt ctatattttt    180
gcaggctcta tcttttttcct gtttctaatt tttctctctt tcagccgatt gggtgatatt   240
aaattagggg cagataccga tgagcctgaa tttggttttg ctcttggat tgcgatgtta    300 ttcgccgccg gaatggggat cgggttaatg tattttgggg tagcagaacc tatttttgcat  360
```

```
taccttaaac ccgtccaaca aaatttaact gagccggagc gtatgaaaga agcgatgatg     420
acaacgttct atcattgggg tattcacgct tgggcaattt atggtgtgat tgccttagct     480
cttgctatt  ttggcttcag atataagtta gcactcacta ttcgttccgg attttatccc     540
ttactaaaac atcgtatttc aggcttctgg gggcatttaa ttgatattat tgcccttgt     600
agcacgattt tcggtttaac gactacactt ggctttgggg tgatgcaggt cagtgctggc     660
tttaacaatc taggtttaat tgaacagagc aattttactg ttcttgcgat tatcgtaaca     720
gtagcaatgg ctcttgccgt gttatctgcc gtttcgggcg taggcaaagg ggttaaaatc     780
ttaagtgaaa tcaatctcac attagccgga ttgctactta tttttgtgat aatcaccggc     840
ccaactctat tacttttctc aagcttcacc gaaaatttag ctattatttt tagctcgctg     900
cttgagatga gtttccgtac cttcgcttat gaaccggaac atcaaggctg gctaagcggc     960
tggacggtcc tttattgggc atggtgggca tcttgggcgc catttgttgg tttgtttatt    1020
gccaagatct ctaaaggcag aaccattcgt gaatttatttt taggggtgct atttgttcca    1080
tcgctgttta acatttttatg gatgaccagc ttcggcagct ctgccatttg gttcgatcaa    1140
caaactgccg gtgctttagc tgaagtcagc ggcaataccg aacaactgtt atttaccttt    1200
tttgagcaat taccgtttgg ctctattgcc tctttcgttg ccgtcattgt tatcagtatt    1260
ttctttatca cctctgccga ctcggggatt tttgttctca acagcattgc ttcacaaggc    1320
gaagaaaatg caccgaaatg gcaaagcgtg cttttgggga gcattattag catcttagcg    1380
ttatcactac tctattcggg tggcttggct tctctgcaaa caatgacact gattatcgcc    1440
ttaccatttta ccttcattat gctgattctc tgtatcggct tatggaaagg attaatggta    1500
gataaccaat acttcaacaa aaaattctcg caaggtagcc aacattgggc gggtaaagat    1560
tggaaacaac gcttggagaa aatcatcaac ccaagcaata gcaagatgt ccgtcacttc     1620
tttattaaag ttgccagacc agcatttta gaacttatcg aggaatttga aagctatggc     1680
ttaatcgcta aaatgaattt caccaacgaa caaaacccga aattagagtt tgaagtggtg    1740
aaagaaaatt tacgcaattt catttacggc attgaaagtg tgccacggga attatcggat    1800
ttggtggtag gtgacgacaa cctaccgaac attgagcaaa ataccatttta cgagccgatt    1860
acttatttct tagacgggcg gaaaggttat gatgtgcaat atatgaccaa agaagagttg    1920
attgccgacg tgctgcaaca gtatgaacgc tttatcaatt tagcgatgga caactcgcac    1980
gacttaatga cggctgattt caatcac                                        2007
```

<210> SEQ ID NO 13
<211> LENGTH: 669
<212> TYPE: PRT
<213> ORGANISM: Artificial Sequence
<220> FEATURE:
<223> OTHER INFORMATION: translation of seq ID NO: 12

<400> SEQUENCE: 13

Leu Asp Leu Ile Lys Lys Leu Asn Thr Gly Ser Thr Phe Arg Val Pro
1               5                   10                  15

Ile Phe Leu Pro Ser Leu Leu Phe Val Ser Phe Val Ala Val Phe Cys
            20                  25                  30

Ile Ile Phe Pro Gln Gln Ala Gln Thr Ser Leu Asp Thr Ile Lys Asn
        35                  40                  45

Ser Leu Phe Gln His Phe Ser Trp Tyr Ile Phe Ala Gly Ser Ile
    50                  55                  60

Phe Phe Leu Phe Leu Ile Phe Leu Ser Phe Ser Arg Leu Gly Asp Ile

```
                65                  70                  75                  80
Lys Leu Gly Ala Asp Thr Asp Glu Pro Glu Phe Gly Phe Gly Ser Trp
                    85                  90                  95
Ile Ala Met Leu Phe Ala Ala Gly Met Gly Ile Gly Leu Met Tyr Phe
                   100                 105                 110
Gly Val Ala Glu Pro Ile Leu His Tyr Leu Lys Pro Val Gln Gln Asn
                   115                 120                 125
Leu Thr Glu Pro Glu Arg Met Lys Glu Ala Met Met Thr Thr Phe Tyr
            130                 135                 140
His Trp Gly Ile His Ala Trp Ala Ile Tyr Gly Val Ile Ala Leu Ala
145                 150                 155                 160
Leu Ala Tyr Phe Gly Phe Arg Tyr Lys Leu Ala Leu Thr Ile Arg Ser
                    165                 170                 175
Gly Phe Tyr Pro Leu Leu Lys His Arg Ile Ser Gly Phe Trp Gly His
                    180                 185                 190
Leu Ile Asp Ile Ile Ala Leu Cys Ser Thr Ile Phe Gly Leu Thr Thr
                    195                 200                 205
Thr Leu Gly Phe Gly Val Met Gln Val Ser Ala Gly Phe Asn Asn Leu
            210                 215                 220
Gly Leu Ile Glu Gln Ser Asn Phe Thr Val Leu Ala Ile Val Thr
225                 230                 235                 240
Val Ala Met Ala Leu Ala Val Leu Ser Ala Val Ser Gly Val Gly Lys
                    245                 250                 255
Gly Val Lys Ile Leu Ser Glu Ile Asn Leu Thr Leu Ala Gly Leu Leu
                    260                 265                 270
Leu Ile Phe Val Ile Ile Thr Gly Pro Thr Leu Leu Leu Phe Ser Ser
                    275                 280                 285
Phe Thr Glu Asn Leu Gly Tyr Tyr Phe Ser Ser Leu Leu Glu Met Ser
            290                 295                 300
Phe Arg Thr Phe Ala Tyr Glu Pro Glu His Gln Gly Trp Leu Ser Gly
305                 310                 315                 320
Trp Thr Val Leu Tyr Trp Ala Trp Trp Ala Ser Trp Ala Pro Phe Val
                    325                 330                 335
Gly Leu Phe Ile Ala Lys Ile Ser Lys Gly Arg Thr Ile Arg Glu Phe
                    340                 345                 350
Ile Leu Gly Val Leu Phe Val Pro Ser Leu Phe Asn Ile Leu Trp Met
                    355                 360                 365
Thr Ser Phe Gly Ser Ser Ala Ile Trp Phe Asp Gln Gln Thr Ala Gly
            370                 375                 380
Ala Leu Ala Glu Val Ser Gly Asn Thr Glu Gln Leu Leu Phe Thr Phe
385                 390                 395                 400
Phe Glu Gln Leu Pro Phe Gly Ser Ile Ala Ser Phe Val Ala Val Ile
                    405                 410                 415
Val Ile Ser Ile Phe Phe Ile Thr Ser Ala Asp Ser Gly Ile Phe Val
                    420                 425                 430
Leu Asn Ser Ile Ala Ser Gln Gly Glu Glu Asn Ala Pro Lys Trp Gln
                    435                 440                 445
Ser Val Leu Trp Gly Ala Leu Leu Ala Ile Leu Ala Leu Ser Leu Leu
                    450                 455                 460
Tyr Ser Gly Gly Leu Ala Ser Leu Gln Thr Met Thr Leu Ile Ile Ala
465                 470                 475                 480
Leu Pro Phe Thr Phe Ile Met Leu Ile Leu Cys Ile Gly Leu Trp Lys
                    485                 490                 495
```

```
Gly Leu Met Val Asp Asn Gln Tyr Phe Asn Lys Lys Phe Ser Gln Gly
            500                 505                 510

Ser Gln His Trp Ala Gly Lys Asp Trp Lys Gln Arg Leu Glu Lys Ile
        515                 520                 525

Ile Asn Pro Ser Asn Lys Gln Asp Val Arg His Phe Ile Lys Val
    530                 535                 540

Ala Arg Pro Ala Phe Leu Glu Leu Ile Glu Glu Phe Glu Ser Tyr Gly
545                 550                 555                 560

Leu Ile Ala Lys Met Asn Phe Thr Asn Glu Gln Asn Pro Lys Leu Glu
                565                 570                 575

Phe Glu Val Val Lys Glu Asn Leu Arg Asn Phe Ile Tyr Gly Ile Glu
            580                 585                 590

Ser Val Pro Arg Glu Leu Ser Asp Leu Val Val Gly Asp Asp Asn Leu
        595                 600                 605

Pro Asn Ile Glu Gln Asn Thr Ile Tyr Glu Pro Ile Thr Tyr Phe Leu
    610                 615                 620

Asp Gly Arg Lys Gly Tyr Asp Val Gln Tyr Met Thr Lys Glu Glu Leu
625                 630                 635                 640

Ile Ala Asp Val Leu Gln Gln Tyr Glu Arg Phe Ile Asn Leu Ala Met
                645                 650                 655

Asp Asn Ser His Asp Leu Met Thr Ala Asp Phe Asn His
            660                 665

<210> SEQ ID NO 14
<211> LENGTH: 4017
<212> TYPE: DNA
<213> ORGANISM: Artificial Sequence
<220> FEATURE:
<223> OTHER INFORMATION: A1 specific gene - IGA specific serine
      metallo-endopeptidase

<400> SEQUENCE: 14
atgaagacca aacatttac tcgttcttat cttgcttctt ttgtaacaat cgtattaagt      60
ttacctgctg tagcatctgt tgtacgtaat gatgtggact atcaatactt ccgcgatttt     120
gccgaaaata aaggaccatt ttcagttggt tcaatgaata ttgatattaa agacaacaat     180
ggacaacttg taggcacgat gcttcataat ttaccaatgg ttgattttag tgctatggta     240
agaggtggat attctacttt aattgcacca caatatttag ttagtgttgc acataatact     300
ggatataaaa tgttcaatt tggtgctgca ggttataacc ctgattcaca tcactatact     360
tataaaattg ttgaccgcaa tgattatgaa aaggttcaag agggttgcca cccagactat     420
catactcctc gattaaataa attagtaaca gaagttgtgc ctgccgcagt caccaatgca     480
ggtacatcta ttaaacccta cttaaatgaa gaacgcttcc ctatgtttct tcgtgctggt     540
tcagggacac aagcgctaag aggaaaagaa agtaataaaa caactggaat cgctggtgct     600
tatgaatatc ttactggcgg taccacatta caattatcta aaagctcccc tgatcactgg     660
ttagattatt caagtaacct ttatcaagta agctatggac acttttcaac ctatgcacta     720
cctggtgata gtggttcagg ttcttacgcc tatgatatga cgaaaaacg atgggtatta     780 gttggtgtgc tcaatttcta taatggtatg gataatcaat tcaaccgctc tgcgattatc     840
cgtaaagatt tccacgagaa aaaatttgcc gaagatattg caggaacaat caataatacc     900
gtacaaaatg cacaattcaa ttggactgct caaggtaaat ccagctctct tagtcaatca     960
aataatgtgc aaaaactcaa cgttgatcta aaagatagta gcattgcaaa ccaaaacact    1020
```

```
tctctgccac aagaaaatca cggtaaaacc attaatttta atggtaaaga tgcaactatt    1080
gtactaaaac aggatattga ccaaggtgca ggtgcattaa atctgaacgc taatctcact    1140
attcgtcctg aaacagacca aacttggcaa ggtgcaggta ttatcgtcgg taaagataaa    1200
aaagtgaatt ggcaagtaaa aaatccacaa ggcgatcgtt tatctaaact cggggaagga    1260
acactctatg taaatggacg tggacagaat cttggcgata tcagtgtagg tgatggtatt    1320
gtaatactta accagcaagc cgatcaccaa ggaagaaaac aggcctttaa tacagtagga    1380
atcgtaagtg gtcgccccac tgttgtgcta ggtagtgcag atcaagttaa tcccgataat    1440
atttactttg gatttcgcgg aggtcgttta gacctaaacg gtaacagcat cgcctttaaa    1500
cgtattcaaa acagcgataa acatgctcgt attgtaaacc acaatcgcga tcacatttct    1560
accttaataa tacaaggcca agatcctctc actagtaatg atcttatatg gggaaaatgg    1620
gcaagtaata gcccagcaga catttacgaa tataccaatc cttatcaaaa taaacgcaaa    1680
gattacttcc gtctgaaagg taattcgaga gtatattatc caacgaatgc tacaagtaac    1740
gatcactggg aatttctttc cagtaaccgc gagcaagcaa tacagaaaat cctagatgcc    1800
aaaaacttaa gacagcgcta tgacacgttt aatggtttta taggggaaga tgcttccaat    1860
aaaactaatg ggatattaaa tgtcgtgttt gatacaaaaa cagaagtaaa tacagaacaa    1920
gataaattaa agaatatcta cacaatgtcg ggaggattta accttaatgg tgaactcacc    1980
cttaaaggtg gtacattgtt gcttctggt cacccaacgc cacacgctta tgatattaag    2040
aataagcatg atgttgtgcg tgaaaacgat tggcaagaca gccatttttac tgctaaaaat    2100 atcacggtaa ataaaatggc acaactctat atcgggagaa atgtcaatga agtaaatagt    2160
cactttactg cgactgataa agccaaactc aatttaggat ttattaatcg ttcaacgcca    2220
agttgctatg attctgaata cacaggcact acacattgtg aagtgcaagc ggtcatttcc    2280
gataatattt ttgcaaatct agcaacaacc gccattaaag gtaatgttaa attacaaaac    2340
catagccaat taaatttagg caaagcaaac ctcactggtt ctgtacaagc tgatcaaaca    2400
actcatatca ctttagcaaa tcacagtcac tggttaaaca atggtacgag ccagattggg    2460
catcttacaa tggaaaaagg gtcgatcctt agcctaaacg ataaatttgc taccacggaa    2520
atcccagtcc gattcaacaa gatgatcatc caaggtaatc taaaaggtaa tggacgaatt    2580
aactataccg caaatttagc caagggcgaa tctgatcatc tccaagttga cggtattgct    2640
gaaggaaatt ttgtccttgc cgttagaaat agcacaactg aagcaaatcc aaaaagctca    2700
ttaaacctac taagcttaaa aaatagcaac caagaaggca ataaagcttc tatttctcta    2760
gaaaataatt atgttgatct aggtacttat cgttatgtat tagaaaatcg taatcacaat    2820
taccatttat ttaatccatt aataccaaat tcaacctcta aagagatgaa tgctacatct    2880
gtatcctcta ttccaaaaaa ggaatctgtt actaatgttc ctactttaga taagaaagaa    2940
actgaacaaa atcttactca actacaaaaa gattttttcag cacaccaatt agaaaatcaa    3000
aaagcaaaac aatctatgat aaatgctcaa tctgagctaa gacgactcaa ttcacaactg    3060
aatgtattgc aaaaatatgt gaattctcgt cgcttaggtt actatactca gcaggcagtt    3120
ttagaacaaa ttagcattat tcaaaataaa attaaacaaa cacaaacaat atttaatgac    3180
gctaatgcaa ctgtaaaact cacagatcaa aagctagaag aagccaaatt agctctaggc    3240
tctgtaaacg atcttgtatt aataaaagcc tctgctccag caatgcaagc aactaatcaa    3300
gatacgagta tgatgaatat tattcaagca gattggaataa gccaatacgc taacacagca    3360
ctttctgaac tctcggcaca ggctaattct gctctgcaaa tcagtaatag cttagatcgc    3420
```

```
caactcttca acaaagcga taaattcaac gtatggagca gcgtcgaaca tcagaaaacc    3480
gagcataaat cagatttata ccgcccgtat aaacaacaaa ccaacctgac ccaactgggc    3540
atacaaatgc cgatagataa cggtttaatg tttggagttg cattatctaa aaaccacgct    3600
aacgcggaat taacgaggg tgtaaacggt aaatcgaatc tactaatggc aagcctatat    3660
ggtaagtggc aatctcaaca aggcactttt atcagccttg atggcagcta cggtaaagca    3720
aaaaaccaac tctacctatt tggtgaaaac cactttaccc gccgaatttc ctctattggt    3780
gctaacattg acatcaatt tgacctcgca ggagttcaaa ttcagccaac aataggagca    3840
agatactacc atttcagcgg ccaagactat acactaggag gagcgaaaat cagctcacca    3900
aatacccact ttatgacata tcaagcgggt ctaaaagcta gtaaaacttt tcattggatg    3960
actggaaagt tgaaccaagc attacaaccc actatgtgga tgcaagtaac aaacgct      4017
```

<210> SEQ ID NO 15
<211> LENGTH: 1339
<212> TYPE: PRT
<213> ORGANISM: Artificial Sequence
<220> FEATURE:
<223> OTHER INFORMATION: translation of seq ID NO:14

<400> SEQUENCE: 15

```
Met Lys Thr Lys Thr Phe Thr Arg Ser Tyr Leu Ala Ser Phe Val Thr
1               5                   10                  15

Ile Val Leu Ser Leu Pro Ala Val Ala Ser Val Val Arg Asn Asp Val
            20                  25                  30

Asp Tyr Gln Tyr Phe Arg Asp Phe Ala Glu Asn Lys Gly Pro Phe Ser
        35                  40                  45

Val Gly Ser Met Asn Ile Asp Ile Lys Asp Asn Asn Gly Gln Leu Val
    50                  55                  60

Gly Thr Met Leu His Asn Leu Pro Met Val Asp Phe Ser Ala Met Val
65                  70                  75                  80

Arg Gly Gly Tyr Ser Thr Leu Ile Ala Pro Gln Tyr Leu Val Ser Val
                85                  90                  95

Ala His Asn Thr Gly Tyr Lys Asn Val Gln Phe Gly Ala Ala Gly Tyr
            100                 105                 110

Asn Pro Asp Ser His His Tyr Thr Tyr Lys Ile Val Asp Arg Asn Asp
        115                 120                 125

Tyr Glu Lys Val Gln Gly Gly Leu His Pro Asp Tyr His Thr Pro Arg
    130                 135                 140

Leu Asn Lys Leu Val Thr Glu Val Val Pro Ala Ala Val Thr Asn Ala
145                 150                 155                 160

Gly Thr Ser Ile Lys Pro Tyr Leu Asn Glu Glu Arg Phe Pro Met Phe
                165                 170                 175

Leu Arg Ala Gly Ser Gly Thr Gln Ala Leu Arg Gly Lys Glu Ser Asn
            180                 185                 190

Lys Thr Thr Gly Ile Ala Gly Ala Tyr Glu Tyr Leu Thr Gly Gly Thr
        195                 200                 205

Thr Leu Gln Leu Ser Lys Ser Ser Pro Asp His Trp Leu Asp Tyr Ser
    210                 215                 220

Ser Asn Leu Tyr Gln Val Ser Tyr Gly Pro Leu Ser Thr Tyr Ala Leu
225                 230                 235                 240

Pro Gly Asp Ser Gly Ser Gly Ser Tyr Ala Tyr Asp Met Asn Glu Lys
                245                 250                 255
```

-continued

```
Arg Trp Val Leu Val Gly Val Leu Asn Phe Tyr Asn Gly Met Asp Asn
            260                 265                 270

Gln Phe Asn Arg Ser Ala Ile Ile Arg Lys Asp Phe His Glu Lys Lys
            275                 280                 285

Phe Ala Glu Asp Ile Ala Gly Thr Ile Asn Asn Thr Val Gln Asn Ala
290                 295                 300

Gln Phe Asn Trp Thr Ala Gln Gly Lys Ser Ser Leu Ser Gln Ser
305                 310                 315                 320

Asn Asn Val Gln Lys Leu Asn Val Asp Leu Lys Asp Ser Ser Ile Ala
            325                 330                 335

Asn Gln Asn Thr Ser Leu Pro Gln Glu Asn His Gly Lys Thr Ile Asn
            340                 345                 350

Phe Asn Gly Lys Asp Ala Thr Ile Val Leu Lys Gln Asp Ile Asp Gln
            355                 360                 365

Gly Ala Gly Ala Leu Asn Leu Asn Ala Asn Leu Thr Ile Arg Pro Glu
370                 375                 380

Thr Asp Gln Thr Trp Gln Gly Ala Gly Ile Ile Val Gly Lys Asp Lys
385                 390                 395                 400

Lys Val Asn Trp Gln Val Lys Asn Pro Gln Gly Asp Arg Leu Ser Lys
            405                 410                 415

Leu Gly Glu Gly Thr Leu Tyr Val Asn Gly Arg Gly Gln Asn Leu Gly
            420                 425                 430

Asp Ile Ser Val Gly Asp Gly Ile Val Ile Leu Asn Gln Gln Ala Asp
            435                 440                 445

His Gln Gly Arg Lys Gln Ala Phe Asn Thr Val Gly Ile Val Ser Gly
            450                 455                 460

Arg Pro Thr Val Val Leu Gly Ser Ala Asp Gln Val Asn Pro Asp Asn
465                 470                 475                 480

Ile Tyr Phe Gly Phe Arg Gly Arg Leu Asp Leu Asn Gly Asn Ser
            485                 490                 495

Ile Ala Phe Lys Arg Ile Gln Asn Ser Asp Lys His Ala Arg Ile Val
            500                 505                 510

Asn His Asn Arg Asp His Ile Ser Thr Leu Ile Ile Gln Gly Gln Asp
            515                 520                 525

Pro Leu Thr Ser Asn Asp Leu Ile Trp Gly Lys Trp Ala Ser Asn Ser
            530                 535                 540

Pro Ala Asp Ile Tyr Glu Tyr Thr Asn Pro Tyr Gln Asn Lys Arg Lys
545                 550                 555                 560

Asp Tyr Phe Arg Leu Lys Gly Asn Ser Arg Val Tyr Tyr Pro Thr Asn
            565                 570                 575

Ala Thr Ser Asn Asp His Trp Glu Phe Leu Ser Ser Asn Arg Glu Gln
            580                 585                 590

Ala Ile Gln Lys Ile Leu Asp Ala Lys Asn Leu Arg Gln Arg Tyr Asp
            595                 600                 605

Thr Phe Asn Gly Phe Ile Gly Glu Asp Ala Ser Asn Lys Thr Asn Gly
            610                 615                 620

Ile Leu Asn Val Val Phe Asp Thr Lys Thr Glu Val Asn Thr Glu Gln
625                 630                 635                 640

Asp Lys Leu Lys Asn Ile Tyr Thr Met Ser Gly Gly Phe Asn Leu Asn
            645                 650                 655

Gly Glu Leu Thr Leu Lys Gly Gly Thr Leu Leu Leu Ser Gly His Pro
            660                 665                 670

Thr Pro His Ala Tyr Asp Ile Lys Asn Lys His Asp Val Val Arg Glu
```

675                 680                 685
Asn Asp Trp Gln Asp Ser His Phe Thr Ala Lys Asn Ile Thr Val Asn
690                 695                 700
Lys Met Ala Gln Leu Tyr Ile Gly Arg Asn Val Asn Glu Val Asn Ser
705                 710                 715                 720
His Phe Thr Ala Thr Asp Lys Ala Lys Leu Asn Leu Gly Phe Ile Asn
                725                 730                 735
Arg Ser Thr Pro Ser Cys Tyr Asp Ser Glu Tyr Thr Gly Thr Thr His
                740                 745                 750
Cys Glu Val Gln Ala Val Ile Ser Asp Asn Ile Phe Ala Asn Leu Ala
                755                 760                 765
Thr Thr Ala Ile Lys Gly Asn Val Lys Leu Gln Asn His Ser Gln Leu
770                 775                 780
Asn Leu Gly Lys Ala Asn Leu Thr Gly Ser Val Gln Ala Asp Gln Thr
785                 790                 795                 800
Thr His Ile Thr Leu Ala Asn His Ser His Trp Leu Asn Asn Gly Thr
                805                 810                 815
Ser Gln Ile Gly His Leu Thr Met Glu Lys Gly Ser Ile Leu Ser Leu
                820                 825                 830
Asn Asp Lys Phe Ala Thr Thr Glu Ile Pro Val Arg Phe Asn Lys Met
                835                 840                 845
Ile Ile Gln Gly Asn Leu Lys Gly Asn Gly Arg Ile Asn Tyr Thr Ala
850                 855                 860
Asn Leu Ala Lys Gly Glu Ser Asp His Leu Gln Val Asp Gly Ile Ala
865                 870                 875                 880
Glu Gly Asn Phe Val Leu Ala Val Arg Asn Ser Thr Thr Glu Ala Asn
                885                 890                 895
Pro Lys Ser Ser Leu Asn Leu Leu Ser Leu Lys Asn Ser Asn Gln Glu
                900                 905                 910
Gly Asn Lys Ala Ser Ile Ser Leu Glu Asn Asn Tyr Val Asp Leu Gly
                915                 920                 925
Thr Tyr Arg Tyr Val Leu Glu Asn Arg Asn His Asn Tyr His Leu Phe
930                 935                 940
Asn Pro Leu Ile Pro Asn Ser Thr Ser Lys Glu Met Asn Ala Thr Ser
945                 950                 955                 960
Val Ser Ser Ile Pro Lys Lys Glu Ser Val Thr Asn Val Pro Thr Leu
                965                 970                 975
Asp Lys Lys Glu Thr Glu Gln Asn Leu Thr Gln Leu Gln Lys Asp Phe
                980                 985                 990
Ser Ala His Gln Leu Glu Asn Gln Lys Ala Lys Gln Ser Met Ile Asn
                995                 1000                1005
Ala Gln Ser Glu Leu Arg Arg Leu Asn Ser Gln Leu Asn Val Leu
        1010                1015                1020
Gln Lys Tyr Val Asn Ser Arg Arg Leu Gly Tyr Tyr Thr Gln Gln
        1025                1030                1035
Ala Val Leu Glu Gln Ile Ser Ile Ile Gln Asn Lys Ile Lys Gln
        1040                1045                1050
Thr Gln Thr Ile Phe Asn Asp Ala Asn Ala Thr Val Lys Leu Thr
        1055                1060                1065
Asp Gln Lys Leu Glu Glu Ala Lys Leu Ala Leu Gly Ser Val Asn
        1070                1075                1080
Asp Leu Val Leu Ile Lys Ala Ser Ala Pro Ala Met Gln Ala Thr
        1085                1090                1095

```
Asn Gln Asp Thr Ser Met Met Asn Ile Ile Gln Ala Asp Trp Ile
    1100                1105                1110

Ser Gln Tyr Ala Asn Thr Ala Leu Ser Glu Leu Ser Ala Gln Ala
    1115                1120                1125

Asn Ser Ala Leu Gln Ile Ser Asn Ser Leu Asp Arg Gln Leu Phe
    1130                1135                1140

Lys Gln Ser Asp Lys Phe Asn Val Trp Ser Ser Val Glu His Gln
    1145                1150                1155

Lys Thr Glu His Lys Ser Asp Leu Tyr Arg Pro Tyr Lys Gln Gln
    1160                1165                1170

Thr Asn Leu Thr Gln Leu Gly Ile Gln Met Pro Ile Asp Asn Gly
    1175                1180                1185

Leu Met Phe Gly Val Ala Leu Ser Lys Asn His Ala Asn Ala Glu
    1190                1195                1200

Phe Asn Glu Gly Val Asn Gly Lys Ser Asn Leu Leu Met Ala Ser
    1205                1210                1215

Leu Tyr Gly Lys Trp Gln Ser Gln Gln Gly Thr Phe Ile Ser Leu
    1220                1225                1230

Asp Gly Ser Tyr Gly Lys Ala Lys Asn Gln Leu Tyr Leu Phe Gly
    1235                1240                1245

Glu Asn His Phe Thr Arg Arg Ile Ser Ser Ile Gly Ala Asn Ile
    1250                1255                1260

Gly His Gln Phe Asp Leu Ala Gly Val Gln Ile Gln Pro Thr Ile
    1265                1270                1275

Gly Ala Arg Tyr Tyr His Phe Ser Gly Gln Asp Tyr Thr Leu Gly
    1280                1285                1290

Gly Ala Lys Ile Ser Ser Pro Asn Thr His Phe Met Thr Tyr Gln
    1295                1300                1305

Ala Gly Leu Lys Ala Ser Lys Thr Phe His Trp Met Thr Gly Lys
    1310                1315                1320

Leu Asn Gln Ala Leu Gln Pro Thr Met Trp Met Gln Val Thr Asn
    1325                1330                1335

Ala
```

<210> SEQ ID NO 16
<211> LENGTH: 2354
<212> TYPE: DNA
<213> ORGANISM: Artificial Sequence
<220> FEATURE:
<223> OTHER INFORMATION: Complete deltaLKTCA with original RBS

<400> SEQUENCE: 16

```
gcattgaatt gatcaactaa tacttggttt ttcaagtgag ttgcaatgcc taaaccatca      60
ccaaaatagt ttggattatt gattttctcc cctacaaaat ctagcccttc gtgttttctt     120
gccatctcag ccaataccgg cacatcgcca aaaatagcat caattcgccc attttgcaca     180
tctaaaatag cattttgata agaggcataa gatttcacat tgtactcttt tttctctttt     240
gctaaatagt gttggtaagt agtcccattt tgcacaccaa tcgttttcac cttagcaaaa     300
tctgtatctt ttttcgcaat gaaggcagca gagcttggaa agtaaggctc gctaaataat     360
acttgtttct tacgtggttc cgtaataccc atacctgaaa ttgcagcatc aaattgtttt     420
tgttttaggc tttggattaa gctatcaaaa ggttggctat ggaatgtaca atttgcattc     480
atctctttac agatagcatt tgcaatatcc acatcaaaac cgataatttc tcccttctct     540
```

| | |
|---|---|
| tcggtcattt caaatggagg atagcttggc tccatcacaa atttgatatc ttgtgcctgc | 600 |
| gcagtaacca cacacccgaa taaaagggtc aaaagtgttt ttttcataaa aagtccctgt | 660 |
| gttttcatta taaggattac cactttaacg cagttacttt cttaaaaaaa gtcttctttt | 720 |
| cataaagttt gttttatgtc atacaaacac atcaaattga gatgtagttt ctcaatcctc | 780 |
| ttgattcctc tatctcaaaa aaacaaccca aaagaaaaaa gaaagtata tgttacatta | 840 |
| atattacaat gtaattattt tgtttaattt ccctacattt tgtataactt taaaacactc | 900 |
| cttttttctct tctgattata taaaagacaa aaaatacaat ttaagctaca aaaaacaaca | 960 |
| aaaacaaca aaaacacga caataagatc gagtaatgat tatattatgt tataatttt | 1020 |
| gacctaattt agaataatta tcgagtccaa attatgaatc aattgaaagc tgttgaagaa | 1080 |
| attatcggta catcacataa cgatatcttt aaaggtagta agttcaatga tgcctttaac | 1140 |
| ggtggtgatg gtgtcgatac tattgacggt aacgacggca atgaccgctt atttggtggt | 1200 |
| aaaggcgatg atattctcga tggtggaaat ggtgatgatt ttatcgatgg cggtaaaggc | 1260 |
| aacgacctat tacacggtgg caagggcgat gatattttcg ttcaccgtaa aggcgatggt | 1320 |
| aatgatatta ttaccgattc tgacggcaat gataaattat cattctctga ttcgaactta | 1380 |
| aaagatttaa catttgaaaa agttaaacat aatcttgtca tcacgaatag caaaaaagag | 1440 |
| aaagtgacca ttcaaaactg gttccgagag gctgattttg ctaaagaagt gcctaattat | 1500 |
| aaagcaacta aagatgagaa aatcgaagaa atcatcggtc aaaatggcga gcggatcacc | 1560 |
| tcaaagcaag ttgatgatct tatcgcaaaa ggtaacggca aaattaccca agatgagcta | 1620 |
| tcaaagttg ttgataacta tgaattgctc aaacatagca aaaatgtgac aaacagctta | 1680 |
| gataagttaa tctcatctgt aagtgcattt acctcgtcta atgattcgag aaatgtatta | 1740 |
| gtggctccaa cttcaatgtt ggatcaaagt ttatcttctc ttcaatttgc tagagcagct | 1800 |
| taatttttaa tgattggcaa ctctatattg tttcacacat tatagagttg ccgttttatt | 1860 |
| ttataaaagg agacaaatatg gaagctaacc atcaaaggaa tgatcttggt ttagttgccc | 1920 |
| tcactatgtt ggcacaatac cataatattt cgcttaatcc ggaagaaata aaacataaat | 1980 |
| ttgatcttga cggaaaaggg cttttcttta ctgcttggct tttagctgca aaatcgttag | 2040 |
| cgttgaaagc gaaacacatt aaaaagagaa tttcccgctt cacttggtg aatttaccgg | 2100 |
| cattagtttg gcaagataac ggtaaacatt ttttattggt aaaagtggat accgataata | 2160 |
| accgctattt aacttacaat ttggaacaag atgctccaca aattctgtca caagacgaat | 2220 |
| tgaagcctg ctatcaaggg cagttaattt tggtcacgtc cagagcttcc gtagtaggtc | 2280 |
| aattagcaaa gttcgatttc acctggttta ttccggcggt gatcaaatac cgaaaaatct | 2340 |
| ttctagaaac cttg | 2354 |

<210> SEQ ID NO 17
<211> LENGTH: 2354
<212> TYPE: DNA
<213> ORGANISM: Artificial Sequence
<220> FEATURE:
<223> OTHER INFORMATION: Complete deltalktCA (with consensus RBS)

<400> SEQUENCE: 17

| | |
|---|---|
| gcattgaatt gatcaactaa tacttggttt ttcaagtgag ttgcaatgcc taaaccatca | 60 |
| ccaaaatagt ttggattatt gattttctcc cctacaaaat ctagcccttc gtgttttctt | 120 |
| gccatctcag ccaataccgg cacatcgcca aaaatagcat caattcgccc attttgcaca | 180 |
| tctaaaatag cattttgata agaggcataa gatttcacat tgtactcttt tttctctttt | 240 |

```
gctaaatagt gttggtaagt agtcccattt tgcacaccaa tcgttttcac cttagcaaaa      300
tctgtatctt ttttcgcaat gaaggcagca gagcttggaa agtaaggctc gctaaataat      360
acttgtttct tacgtggttc cgtaataccc atacctgaaa ttgcagcatc aaattgtttt      420
tgttttaggc tttggattaa gctatcaaaa ggttggctat ggaatgtaca atttgcattc      480
atctctttac agatagcatt tgcaatatcc acatcaaaac cgataatttc tcccttctct      540
tcggtcattt caaatggagg atagcttggc tccatcacaa atttgatatc ttgtgcctgc      600
gcagtaacca cacccgaa taaagggtc aaaagtgttt ttttcataaa aagtccctgt         660
gttttcatta taaggattac cactttaacg cagttacttt cttaaaaaaa gtcttctttt      720
cataagtttt gttttatgtc atacaaacac atcaaattga gatgtagttt ctcaatcctc      780
ttgattcctc tatctcaaaa aaacaaccca aagaaaaaa gaaagtata tgttacatta        840 atattacaat gtaattattt tgtttaattt ccctacattt tgtataactt taaaacactc      900 cttttctct tctgattata taaagacaa aaatacaat ttaagctaca aaaacaaca          960 aaaacaaca aaaacacga caataagatc gagtaatgat tatattatgt tataatttt        1020 gacctaattt agaataatta taggaggcaa attatgaatc aattgaaagc tgttgaagaa      1080
attatcggta catcacataa cgatatcttt aaaggtagta agttcaatga tgcctttaac     1140
ggtggtgatg gtgtcgatac tattgacggt aacgacggca atgaccgctt atttggtggt    1200
aaaggcgatg atattctcga tggtggaaat ggtgatgatt ttatcgatgg cggtaaaggc    1260
aacgacctat tacacggtgg caagggcgat gatattttcg ttcaccgtaa aggcgatggt    1320
aatgatatta ttaccgattc tgacggcaat gataaattat cattctctga ttcgaactta    1380
aaagatttaa catttgaaaa agttaaacat aatcttgtca tcacgaatag caaaaaagag    1440
aaagtgacca ttcaaaactg gttccgagag gctgattttg ctaaagaagt gcctaattat    1500
aaagcaacta aagatgagaa aatcgaagaa atcatcggtc aaaatggcga gcggatcacc    1560
tcaaagcaag ttgatgatct tatcgcaaaa ggtaacggca aaattaccca agatgagcta    1620
tcaaaagttg ttgataacta tgaattgctc aaacatagca aaaatgtgac aaacagctta    1680
gataagttaa tctcatctgt aagtgcattt acctcgtcta atgattcgag aaatgtatta    1740
gtggctccaa cttcaatgtt ggatcaaagt ttatcttctc ttcaatttgc tagagcagct    1800 taattttttaa tgattggcaa ctctatattg tttcacacat tatagagttg ccgttttatt    1860
ttataaaagg agacaatatg gaagctaacc atcaaaggaa tgatcttggt ttagttgccc    1920
tcactatgtt ggcacaatac cataatattt cgcttaatcc ggaagaaata aaacataaat    1980
ttgatcttga cggaaagg ctttcttta actgcttggct tttagctgca aaatcgttag       2040
cgttgaaagc gaaacacatt aaaaaagaga tttcccgctt acacttggtg aatttaccgg    2100
cattagtttg gcaagataac ggtaaacatt tttattggt aaaagtggat accgataata     2160
accgctattt aacttacaat ttggaacaag atgctccaca aattctgtca caagacgaat    2220
ttgaagcctg ctatcaaggg cagttaattt tggtcacgtc cagagcttcc gtagtaggtc    2280
aattagcaaa gttcgatttc acctggttta ttccggcggt gatcaaatac cgaaaaatct    2340
ttctagaaac cttg                                                        2354
```

<210> SEQ ID NO 18
<211> LENGTH: 249
<212> TYPE: PRT
<213> ORGANISM: Artificial Sequence
<220> FEATURE:

<223> OTHER INFORMATION: Translation of deltaLKTCA

<400> SEQUENCE: 18

Met Asn Gln Leu Lys Ala Val Glu Glu Ile Ile Gly Thr Ser His Asn
1               5                   10                  15

Asp Ile Phe Lys Gly Ser Lys Phe Asn Asp Ala Phe Asn Gly Gly Asp
            20                  25                  30

Gly Val Asp Thr Ile Asp Gly Asn Asp Gly Asn Asp Arg Leu Phe Gly
        35                  40                  45

Gly Lys Gly Asp Asp Ile Leu Asp Gly Gly Asn Gly Asp Asp Phe Ile
    50                  55                  60

Asp Gly Gly Lys Gly Asn Asp Leu Leu His Gly Gly Lys Gly Asp Asp
65                  70                  75                  80

Ile Phe Val His Arg Lys Gly Asp Gly Asn Asp Ile Ile Thr Asp Ser
                85                  90                  95

Asp Gly Asn Asp Lys Leu Ser Phe Ser Asp Ser Asn Leu Lys Asp Leu
            100                 105                 110

Thr Phe Glu Lys Val Lys His Asn Leu Val Ile Thr Asn Ser Lys Lys
        115                 120                 125

Glu Lys Val Thr Ile Gln Asn Trp Phe Arg Glu Ala Asp Phe Ala Lys
    130                 135                 140

Glu Val Pro Asn Tyr Lys Ala Thr Lys Asp Glu Lys Ile Glu Glu Ile
145                 150                 155                 160

Ile Gly Gln Asn Gly Glu Arg Ile Thr Ser Lys Gln Val Asp Asp Leu
                165                 170                 175

Ile Ala Lys Gly Asn Gly Lys Ile Thr Gln Asp Glu Leu Ser Lys Val
            180                 185                 190

Val Asp Asn Tyr Glu Leu Leu Lys His Ser Lys Asn Val Thr Asn Ser
        195                 200                 205

Leu Asp Lys Leu Ile Ser Ser Val Ser Ala Phe Thr Ser Ser Asn Asp
    210                 215                 220

Ser Arg Asn Val Leu Val Ala Pro Thr Ser Met Leu Asp Gln Ser Leu
225                 230                 235                 240

Ser Ser Leu Gln Phe Ala Arg Ala Ala
                245

<210> SEQ ID NO 19
<211> LENGTH: 372
<212> TYPE: DNA
<213> ORGANISM: Artificial Sequence
<220> FEATURE:
<223> OTHER INFORMATION: d153_00985 d153_00985 Leukotoxin-activating
      lysine-acyltransferase lktC serotype A1 (EC 2.3.1.)
      (Toxin-activating protein C) (Leukotoxin C) - LKTC

<400> SEQUENCE: 19
atgctactta tagataacgg tattccgatc gcttattgta gttgggcaga tttaaacctt      60
gagactgagg tgaaatatat taaggatatt aattcgttaa caccagaaga atggcagtct     120
ggtgacagac gctggattat tgattgggta gcaccattcg acattctca attactttat     180 aaaaaaatgt gtcagaaata ccctgatatg atcgtcagat ctatacgctt ttatccaaag    240
cagaaagaat taggcaaaat tgcctacttt aaaggaggta attagataa aaaaacagca     300 aaaaaacgtt ttgatacata tcaagaagag ctggcaacag cacttaaaaa tgaatttaat    360
tttattaaaa aa                                                         372

<210> SEQ ID NO 20
<211> LENGTH: 124
<212> TYPE: PRT
<213> ORGANISM: Artificial Sequence
<220> FEATURE:
<223> OTHER INFORMATION: Translation of SEQ ID 19

<400> SEQUENCE: 20

```
Met Leu Leu Ile Asp Asn Gly Ile Pro Ile Ala Tyr Cys Ser Trp Ala
1               5                   10                  15

Asp Leu Asn Leu Glu Thr Glu Val Lys Tyr Ile Lys Asp Ile Asn Ser
            20                  25                  30

Leu Thr Pro Glu Glu Trp Gln Ser Gly Asp Arg Arg Trp Ile Ile Asp
        35                  40                  45

Trp Val Ala Pro Phe Gly His Ser Gln Leu Leu Tyr Lys Lys Met Cys
    50                  55                  60

Gln Lys Tyr Pro Asp Met Ile Val Arg Ser Ile Arg Phe Tyr Pro Lys
65                  70                  75                  80

Gln Lys Glu Leu Gly Lys Ile Ala Tyr Phe Lys Gly Gly Lys Leu Asp
                85                  90                  95

Lys Lys Thr Ala Lys Lys Arg Phe Asp Thr Tyr Gln Glu Glu Leu Ala
            100                 105                 110

Thr Ala Leu Lys Asn Glu Phe Asn Phe Ile Lys Lys
        115                 120
```

<210> SEQ ID NO 21
<211> LENGTH: 2859
<212> TYPE: DNA
<213> ORGANISM: Artificial Sequence
<220> FEATURE:
<223> OTHER INFORMATION: d153_00984 d153_00984 bifunctional
      hemolysin-adenylate cyclase precursor - LKTA

<400> SEQUENCE: 21

| | | | | | |
|---|---|---|---|---|---|
| atgggaacta | gacttacaac | cctatcaaat | gggctaaaaa | acactttaac | ggcaaccaaa |     60 |
| agtggcttac | ataaagccgg | tcaatcatta | acccaagccg | gcagttcttt | aaaaactggg |    120 |
| gcaaaaaaaa | ttatcctcta | tattccccaa | aattaccaat | atgatactga | acaaggtaat |    180 |
| ggtttacagg | atttagtcaa | agcggccgaa | gagttgggga | ttgaggtaca | aagagaagaa |    240 |
| cgcaataata | ttgcaacagc | tcaaaccagt | ttaggcacga | ttcaaaccgc | tattggctta |    300 |
| actgagcgtg | gcattgtgtt | atccgctcca | caaattgata | aattgctaca | gaaaactaaa |    360 |
| gcaggccaag | cattaggttc | tgccgaaagc | attgtacaaa | atgcaaataa | agccaaaact |    420 |
| gtattatctg | gcattcaatc | tatttttaggc | tcagtattgg | ctggaatgga | tttagatgag |    480 |
| gccttacaga | ataacagcaa | ccaacatgct | cttgctaaag | ctggcttgga | gctaacaaat |    540 |
| tcattaattg | aaaatattgc | taattcagta | aaaacacttg | acgaatttgg | tgagcaaatt |    600 |
| agtcaatttg | gttcaaaact | acaaaatatc | aaaggcttag | gactttagg | agacaaactc |    660 |
| aaaaatatcg | gtggacttga | taaagctggc | cttggtttag | atgttatctc | agggctatta |    720 |
| tcgggcgcaa | cagctgcact | tgtacttgca | gataaaaatg | cttcaacagc | taaaaagtg |    780 |
| ggtgcgggtt | ttgaattggc | aaaccaagtt | gttggtaata | ttaccaaagc | cgtttcttct |    840 |
| tacatttag | cccaacgtgt | tgcagcaggt | ttatcttcaa | ctgggcctgt | ggctgcttta |    900 |
| attgcttcta | ctgttctctct | tgcgattagc | ccattagcat | tgccggtat | tgccgataaa |    960 |
| tttaatcatg | caaaagtttt | agagagttat | gccgaacgct | ttaaaaaatt | aggctatgac |   1020 |
| ggagataatt | tattagcaga | atatcagcgg | ggaacaggga | ctattgatgc | atcggttact |   1080 |

-continued

```
gcaattaata ccgcattggc cgctattgct ggtggtgtgt ctgctgctgc agccggctcg    1140
gttattgctt caccgattgc cttattagta tctgggatta ccgtgtaat ttctacgatt    1200
ctgcaatatt ctaaacaagc aatgtttgag cacgttgcaa ataaaattca taacaaaatt    1260
gtagaatggg aaaaaaataa tcacggtaag aactactttg aaaatggtta cgatgcccgt    1320
tatcttgcga atttacaaga taatatgaaa ttcttactga acttaaacaa agagttacag    1380
gcagaacgtg tcatcgctat tactcagcag caatgggata caacattgg tgatttagct    1440
ggtattagcc gtttaggtga aaaagtcctt agtggtaaag cctatgtgga tgcgtttgaa    1500
gaaggcaaac acattaaagc cgataaatta gtacagttgg attcggcaaa cggtattatt    1560
gatgtgagta attcgggtaa agcgaaaact cagcatatct tattcagaac gccattattg    1620
acgccgggaa cagagcatcg tgaacgcgta caaacaggta aatatgaata tattaccaag    1680
ctcaatatta ccgtgtaga tagctggaaa attacagatg gtgcagcaag ttctaccttt    1740
gatttaacta acgttgttca gcgtattggt attgaattag acaatgctgg aaatgtaact    1800
aaaaccaaag aaacaaaaat tattgccaaa cttggtgaag gtgatgacaa cgtatttgtt    1860
ggttctggta cgacggaaat tgatggcggt gaaggttacg accgagttca ctatagccgt    1920
ggaaactatg gtgctttaac tattgatgca accaaagaga ccgagcaagg tagttatacc    1980
gtaaatcgtt tcgtagaaac cggtaaagca ctacacgaag tgacttcaac ccataccgca    2040
ttagtgggca accgtgaaga aaaatagaa tatcgtcata gcaataacca gcaccatgcc    2100
ggttattaca ccaaagatac cttgaaagct gttgaagaaa ttatcggtac atcacataac    2160
gatatcttta aggtagtaa gttcaatgat gcctttaacg gtggtgatgg tgtcgatact    2220
attgacggta acgacggcaa tgaccgctta tttggtggta aaggcgatga tattctcgat    2280
ggtggaaatg gtgatgattt tatcgatggc ggtaaaggca acgacctatt acacggtggc    2340
aagggcgatg atattttcgt tcaccgtaaa ggcgatggta atgatattat taccgattct    2400
gacggcaatg ataaattatc attctctgat tcgaacttaa aagatttaac atttgaaaaa    2460
gttaaacata atcttgtcat cacgaatagc aaaaaagaga aagtgaccat tcaaaactgg    2520
ttccgagagg ctgattttgc taaagaagtg cctaattata aagcaactaa agatgagaaa    2580
atcgaagaaa tcatcggtca aaatggcgag cggatcacct caaagcaagt tgatgatctt    2640
atcgcaaaag gtaacggcaa aattacccaa gatgagctat caaaagttgt tgataactat    2700
gaattgctca acatagcaa aaatgtgaca aacagcttag ataagttaat ctcatctgta    2760
agtgcattta cctcgtctaa tgattcgaga aatgtattag tggctccaac ttcaatgttg    2820
gatcaaagtt tatcttctct tcaatttgct agagcagct                          2859
```

<210> SEQ ID NO 22
<211> LENGTH: 953
<212> TYPE: PRT
<213> ORGANISM: Artificial Sequence
<220> FEATURE:
<223> OTHER INFORMATION: Translation of SEQ ID 21

<400> SEQUENCE: 22

```
Met Gly Thr Arg Leu Thr Thr Leu Ser Asn Gly Leu Lys Asn Thr Leu
1               5                   10                  15

Thr Ala Thr Lys Ser Gly Leu His Lys Ala Gly Gln Ser Leu Thr Gln
            20                  25                  30

Ala Gly Ser Ser Leu Lys Thr Gly Ala Lys Lys Ile Ile Leu Tyr Ile
        35                  40                  45
```

-continued

```
Pro Gln Asn Tyr Gln Tyr Asp Thr Glu Gln Gly Asn Gly Leu Gln Asp
    50                  55                  60
Leu Val Lys Ala Ala Glu Leu Gly Ile Glu Val Gln Arg Glu Glu
65                  70                  75                  80
Arg Asn Asn Ile Ala Thr Ala Gln Thr Ser Leu Gly Thr Ile Gln Thr
                85                  90                  95
Ala Ile Gly Leu Thr Glu Arg Gly Ile Val Leu Ser Ala Pro Gln Ile
                100                 105                 110
Asp Lys Leu Leu Gln Lys Thr Lys Ala Gly Gln Ala Leu Gly Ser Ala
            115                 120                 125
Glu Ser Ile Val Gln Asn Ala Asn Lys Ala Lys Thr Val Leu Ser Gly
    130                 135                 140
Ile Gln Ser Ile Leu Gly Ser Val Leu Ala Gly Met Asp Leu Asp Glu
145                 150                 155                 160
Ala Leu Gln Asn Asn Ser Asn Gln His Ala Leu Ala Lys Ala Gly Leu
                165                 170                 175
Glu Leu Thr Asn Ser Leu Ile Glu Asn Ile Ala Asn Ser Val Lys Thr
                180                 185                 190
Leu Asp Glu Phe Gly Glu Gln Ile Ser Gln Phe Gly Ser Lys Leu Gln
            195                 200                 205
Asn Ile Lys Gly Leu Gly Thr Leu Gly Asp Lys Leu Lys Asn Ile Gly
    210                 215                 220
Gly Leu Asp Lys Ala Gly Leu Gly Leu Asp Val Ile Ser Gly Leu Leu
225                 230                 235                 240
Ser Gly Ala Thr Ala Ala Leu Val Leu Ala Asp Lys Asn Ala Ser Thr
                245                 250                 255
Ala Lys Lys Val Gly Ala Gly Phe Glu Leu Ala Asn Gln Val Val Gly
                260                 265                 270
Asn Ile Thr Lys Ala Val Ser Ser Tyr Ile Leu Ala Gln Arg Val Ala
            275                 280                 285
Ala Gly Leu Ser Ser Thr Gly Pro Val Ala Ala Leu Ile Ala Ser Thr
    290                 295                 300
Val Ser Leu Ala Ile Ser Pro Leu Ala Phe Ala Gly Ile Ala Asp Lys
305                 310                 315                 320
Phe Asn His Ala Lys Ser Leu Glu Ser Tyr Ala Glu Arg Phe Lys Lys
                325                 330                 335
Leu Gly Tyr Asp Gly Asp Asn Leu Leu Ala Glu Tyr Gln Arg Gly Thr
                340                 345                 350
Gly Thr Ile Asp Ala Ser Val Thr Ala Ile Asn Thr Ala Leu Ala Ala
            355                 360                 365
Ile Ala Gly Gly Val Ser Ala Ala Ala Gly Ser Val Ile Ala Ser
    370                 375                 380
Pro Ile Ala Leu Leu Val Ser Gly Ile Thr Gly Val Ile Ser Thr Ile
385                 390                 395                 400
Leu Gln Tyr Ser Lys Gln Ala Met Phe Glu His Val Ala Asn Lys Ile
                405                 410                 415
His Asn Lys Ile Val Glu Trp Glu Lys Asn Asn His Gly Lys Asn Tyr
                420                 425                 430
Phe Glu Asn Gly Tyr Asp Ala Arg Tyr Leu Ala Asn Leu Gln Asp Asn
            435                 440                 445
Met Lys Phe Leu Leu Asn Leu Asn Lys Glu Leu Gln Ala Glu Arg Val
    450                 455                 460
```

-continued

```
Ile Ala Ile Thr Gln Gln Gln Trp Asp Asn Asn Ile Gly Asp Leu Ala
465                 470                 475                 480

Gly Ile Ser Arg Leu Gly Glu Lys Val Leu Ser Gly Lys Ala Tyr Val
            485                 490                 495

Asp Ala Phe Glu Glu Gly Lys His Ile Lys Ala Asp Lys Leu Val Gln
        500                 505                 510

Leu Asp Ser Ala Asn Gly Ile Ile Asp Val Ser Asn Ser Gly Lys Ala
    515                 520                 525

Lys Thr Gln His Ile Leu Phe Arg Thr Pro Leu Leu Thr Pro Gly Thr
530                 535                 540

Glu His Arg Glu Arg Val Gln Thr Gly Lys Tyr Glu Tyr Ile Thr Lys
545                 550                 555                 560

Leu Asn Ile Asn Arg Val Asp Ser Trp Lys Ile Thr Asp Gly Ala Ala
            565                 570                 575

Ser Ser Thr Phe Asp Leu Thr Asn Val Val Gln Arg Ile Gly Ile Glu
        580                 585                 590

Leu Asp Asn Ala Gly Asn Val Thr Lys Thr Lys Glu Thr Lys Ile Ile
    595                 600                 605

Ala Lys Leu Gly Glu Gly Asp Asp Asn Val Phe Val Gly Ser Gly Thr
610                 615                 620

Thr Glu Ile Asp Gly Gly Glu Gly Tyr Asp Arg Val His Tyr Ser Arg
625                 630                 635                 640

Gly Asn Tyr Gly Ala Leu Thr Ile Asp Ala Thr Lys Glu Thr Glu Gln
            645                 650                 655

Gly Ser Tyr Thr Val Asn Arg Phe Val Glu Thr Gly Lys Ala Leu His
        660                 665                 670

Glu Val Thr Ser Thr His Thr Ala Leu Val Gly Asn Arg Glu Glu Lys
    675                 680                 685

Ile Glu Tyr Arg His Ser Asn Asn Gln His His Ala Gly Tyr Tyr Thr
690                 695                 700

Lys Asp Thr Leu Lys Ala Val Glu Glu Ile Ile Gly Thr Ser His Asn
705                 710                 715                 720

Asp Ile Phe Lys Gly Ser Lys Phe Asn Asp Ala Phe Asn Gly Gly Asp
            725                 730                 735

Gly Val Asp Thr Ile Asp Gly Asn Asp Gly Asn Asp Arg Leu Phe Gly
        740                 745                 750

Gly Lys Gly Asp Asp Ile Leu Asp Gly Gly Asn Gly Asp Asp Phe Ile
    755                 760                 765

Asp Gly Gly Lys Gly Asn Asp Leu Leu His Gly Gly Lys Gly Asp Asp
770                 775                 780

Ile Phe Val His Arg Lys Gly Asp Gly Asn Asp Ile Ile Thr Asp Ser
785                 790                 795                 800

Asp Gly Asn Asp Lys Leu Ser Phe Ser Asp Ser Asn Leu Lys Asp Leu
            805                 810                 815

Thr Phe Glu Lys Val Lys His Asn Leu Val Ile Thr Asn Ser Lys Lys
        820                 825                 830

Glu Lys Val Thr Ile Gln Asn Trp Phe Arg Glu Ala Asp Phe Ala Lys
    835                 840                 845

Glu Val Pro Asn Tyr Lys Ala Thr Lys Asp Glu Lys Ile Glu Glu Ile
850                 855                 860

Ile Gly Gln Asn Gly Glu Arg Ile Thr Ser Lys Gln Val Asp Asp Leu
865                 870                 875                 880

Ile Ala Lys Gly Asn Gly Lys Ile Thr Gln Asp Glu Leu Ser Lys Val
```

|  | 885 |  |  | 890 |  |  |  | 895 |  |  |
|---|---|---|---|---|---|---|---|---|---|---|

Val Asp Asn Tyr Glu Leu Leu Lys His Ser Lys Asn Val Thr Asn Ser
                900                 905                 910

Leu Asp Lys Leu Ile Ser Ser Val Ser Ala Phe Thr Ser Ser Asn Asp
        915                 920                 925

Ser Arg Asn Val Leu Val Ala Pro Thr Ser Met Leu Asp Gln Ser Leu
    930                 935                 940

Ser Ser Leu Gln Phe Ala Arg Ala Ala
945                 950

<210> SEQ ID NO 23
<211> LENGTH: 2124
<212> TYPE: DNA
<213> ORGANISM: Artificial Sequence
<220> FEATURE:
<223> OTHER INFORMATION: d153_00983 d153_00983 ABC-type bacteriocin/
    lantibiotic exporters, contain an N-terminal double-glycine
    peptidase domain - LKTB

<400> SEQUENCE: 23

| | |
|---|---|
| atggaagcta accatcaaag gaatgatctt ggtttagttg ccctcactat gttggcacaa | 60 |
| taccataata tttcgcttaa tccggaagaa ataaaacata atttgatct tgacggaaaa | 120 |
| gggctttctt taactgcttg gctttagct gcaaaatcgt tagcgttgaa agcgaaacac | 180 |
| attaaaaaag agatttcccg cttacacttg gtgaatttac cggcattagt ttggcaagat | 240 |
| aacggtaaac attttttatt ggtaaaagtg ataccgata taaccgcta tttaacttac | 300 |
| aatttggaac aagatgctcc acaaattctg tcacaagacg aatttgaagc ctgctatcaa | 360 |
| gggcagttaa ttttggtcac gtccagagct tccgtagtag gtcaattagc aaagttcgat | 420 |
| ttcacctggt ttattccggc ggtgatcaaa taccgaaaaa tctttctaga aaccttgatt | 480 |
| gtttcgatct ttttgcaaat ttttgcccta attaccgc tattcttcca agttgttatg | 540 |
| gataaagtac tggtgcatcg aggttttttca accttgaata tcattacggt tgccttagct | 600 |
| attgtgatca tctttgaaat tgtactaagt ggtttgagaa cctatgtttt ttctcatagc | 660 |
| actagccgta ttgatgttga attaggcgct aaattatttc gacatttatt atcactaccc | 720 |
| atttcttatt tgaaaacag acgagttgga gatacagtcg ctagggttag agaattagat | 780 |
| caaattcgta atttccttac cggacaagca ttaacctcgg tgttagatct cttattctct | 840 |
| tttatctttt tgccgtaat gtggtattac agcccaaat taaccttggt aattcttggt | 900 |
| tcattgccct gctatatttt atggtcaatt tttattagtc cgatttaag acggcgttta | 960 |
| gatgagaaat tgcccgaag tgctgataac caagcattct tagttgagtc ggtaacagcc | 1020 |
| atcaatatga ttaaagcgat ggcggttgct ccacaaatga cggatacatg gataaacag | 1080 |
| ctggcaagct atgtttcatc aagtttccgt gtcaccgtat tagcaaccat tgggcaacaa | 1140 |
| ggtgtacaac ttattcaaaa aaccgttatg gtgattaacc tttggttagg gcacactta | 1200 |
| gttatttcag gcgatctgag tattgggcaa ttaattgcct taatatgct atcagggcaa | 1260 |
| gtgattgcac cggtgattcg gctggctcag ctctggcaag atttccaaca gttgggatt | 1320 |
| tccgtcactc gctaggtga tgttttaaac tctccaaccg aacaatatca aggcaaatta | 1380 |
| tcactaccag aaataaaagg cgatatctca tttaaaaata tccgctttag atataaacca | 1440 |
| gatgcaccaa ctatttttaaa taatgtgaat ttagaaatta ggcaaggaga agtgattggg | 1500 |
| attgttggac gttccggttc aggcaaaagt actctgacta aattactgca acgtttttat | 1560 |
| attcctgaaa atgggcaggt tttgattgat ggacatgatc tagccttagc tgatccaaac | 1620 |

```
tggctacgcc gtcaaatagg tgtagtgctg caagataatg tgttattaaa ccgcagtatc   1680
cgagaaaata ttgcgctatc agatccagga atgccaatgg agcgagtaat ttatgcagca   1740
aaattagcag gggctcacga ttttatttca gaattgcgtg aaggttataa caccattgtg   1800
ggtgaacaag gagcggggct ttcaggcggg caacgccaac ggattgcgat tgctcgagct   1860
ttggtaaaca acccgaaaat cctgattttt gatgaggcaa ccagtgccct cgattacgaa   1920
tctgagcata ttattatgca aaatatgcaa aaaatatgcc aaggcagaac cgtgattttg   1980
attgcacatc gtttatcgac cgtcaaaaat gcggatcgaa ttattgtgat ggaaaagggg   2040
gaaattgttg agcaaggcaa gcaccacgaa ttactgcaaa acagtaacgg actttattcc   2100
tacttacacc aattacaact taat                                          2124
```

<210> SEQ ID NO 24
<211> LENGTH: 708
<212> TYPE: PRT
<213> ORGANISM: Artificial Sequence
<220> FEATURE:
<223> OTHER INFORMATION: Translation of SEQ ID 23

<400> SEQUENCE: 24

```
Met Glu Ala Asn His Gln Arg Asn Asp Leu Gly Leu Val Ala Leu Thr
1               5                   10                  15

Met Leu Ala Gln Tyr His Asn Ile Ser Leu Asn Pro Glu Glu Ile Lys
            20                  25                  30

His Lys Phe Asp Leu Asp Gly Lys Gly Leu Ser Leu Thr Ala Trp Leu
        35                  40                  45

Leu Ala Ala Lys Ser Leu Ala Leu Lys Ala Lys His Ile Lys Lys Glu
    50                  55                  60

Ile Ser Arg Leu His Leu Val Asn Leu Pro Ala Leu Val Trp Gln Asp
65                  70                  75                  80

Asn Gly Lys His Phe Leu Leu Val Lys Val Asp Thr Asp Asn Asn Arg
                85                  90                  95

Tyr Leu Thr Tyr Asn Leu Glu Gln Asp Ala Pro Gln Ile Leu Ser Gln
            100                 105                 110

Asp Glu Phe Glu Ala Cys Tyr Gln Gly Gln Leu Ile Leu Val Thr Ser
        115                 120                 125

Arg Ala Ser Val Val Gly Gln Leu Ala Lys Phe Asp Phe Thr Trp Phe
    130                 135                 140

Ile Pro Ala Val Ile Lys Tyr Arg Lys Ile Phe Leu Glu Thr Leu Ile
145                 150                 155                 160

Val Ser Ile Phe Leu Gln Ile Phe Ala Leu Ile Thr Pro Leu Phe Phe
                165                 170                 175

Gln Val Val Met Asp Lys Val Leu Val His Arg Gly Phe Ser Thr Leu
            180                 185                 190

Asn Ile Ile Thr Val Ala Leu Ala Ile Val Ile Phe Glu Ile Val
        195                 200                 205

Leu Ser Gly Leu Arg Thr Tyr Val Phe Ser His Ser Thr Ser Arg Ile
    210                 215                 220

Asp Val Glu Leu Gly Ala Lys Leu Phe Arg His Leu Leu Ser Leu Pro
225                 230                 235                 240

Ile Ser Tyr Phe Glu Asn Arg Arg Val Gly Asp Thr Val Ala Arg Val
                245                 250                 255

Arg Glu Leu Asp Gln Ile Arg Asn Phe Leu Thr Gly Gln Ala Leu Thr
            260                 265                 270
```

```
Ser Val Leu Asp Leu Leu Phe Ser Phe Ile Phe Ala Val Met Trp
    275                 280                 285

Tyr Tyr Ser Pro Lys Leu Thr Leu Val Ile Leu Gly Ser Leu Pro Cys
        290                 295                 300

Tyr Ile Leu Trp Ser Ile Phe Ile Ser Pro Ile Leu Arg Arg Arg Leu
305                 310                 315                 320

Asp Glu Lys Phe Ala Arg Ser Ala Asp Asn Gln Ala Phe Leu Val Glu
                325                 330                 335

Ser Val Thr Ala Ile Asn Met Ile Lys Ala Met Ala Val Ala Pro Gln
                340                 345                 350

Met Thr Asp Thr Trp Asp Lys Gln Leu Ala Ser Tyr Val Ser Ser Ser
                355                 360                 365

Phe Arg Val Thr Val Leu Ala Thr Ile Gly Gln Gln Gly Val Gln Leu
    370                 375                 380

Ile Gln Lys Thr Val Met Val Ile Asn Leu Trp Leu Gly Ala His Leu
385                 390                 395                 400

Val Ile Ser Gly Asp Leu Ser Ile Gly Gln Leu Ile Ala Phe Asn Met
                405                 410                 415

Leu Ser Gly Gln Val Ile Ala Pro Val Ile Arg Leu Ala Gln Leu Trp
                420                 425                 430

Gln Asp Phe Gln Gln Val Gly Ile Ser Val Thr Arg Leu Gly Asp Val
                435                 440                 445

Leu Asn Ser Pro Thr Glu Gln Tyr Gln Gly Lys Leu Ser Leu Pro Glu
                450                 455                 460

Ile Lys Gly Asp Ile Ser Phe Lys Asn Ile Arg Phe Arg Tyr Lys Pro
465                 470                 475                 480

Asp Ala Pro Thr Ile Leu Asn Asn Val Asn Leu Glu Ile Arg Gln Gly
                485                 490                 495

Glu Val Ile Gly Ile Val Gly Arg Ser Gly Ser Gly Lys Ser Thr Leu
                500                 505                 510

Thr Lys Leu Leu Gln Arg Phe Tyr Ile Pro Glu Asn Gly Gln Val Leu
    515                 520                 525

Ile Asp Gly His Asp Leu Ala Leu Ala Asp Pro Asn Trp Leu Arg Arg
    530                 535                 540

Gln Ile Gly Val Val Leu Gln Asp Asn Val Leu Leu Asn Arg Ser Ile
545                 550                 555                 560

Arg Glu Asn Ile Ala Leu Ser Asp Pro Gly Met Pro Met Glu Arg Val
                565                 570                 575

Ile Tyr Ala Ala Lys Leu Ala Gly Ala His Asp Phe Ile Ser Glu Leu
                580                 585                 590

Arg Glu Gly Tyr Asn Thr Ile Val Gly Glu Gln Gly Ala Gly Leu Ser
    595                 600                 605

Gly Gly Gln Arg Gln Arg Ile Ala Ile Ala Arg Ala Leu Val Asn Asn
610                 615                 620

Pro Lys Ile Leu Ile Phe Asp Glu Ala Thr Ser Ala Leu Asp Tyr Glu
625                 630                 635                 640

Ser Glu His Ile Ile Met Gln Asn Met Gln Lys Ile Cys Gln Gly Arg
                645                 650                 655

Thr Val Ile Leu Ile Ala His Arg Leu Ser Thr Val Lys Asn Ala Asp
                660                 665                 670

Arg Ile Ile Val Met Glu Lys Gly Glu Ile Val Glu Gln Gly Lys His
    675                 680                 685
```

His Glu Leu Leu Gln Asn Ser Asn Gly Leu Tyr Ser Tyr Leu His Gln
    690                 695                 700

Leu Gln Leu Asn
705

<210> SEQ ID NO 25
<211> LENGTH: 1434
<212> TYPE: DNA
<213> ORGANISM: Artificial Sequence
<220> FEATURE:
<223> OTHER INFORMATION: d153_00982 d153_00982 Microcin H47 secretion
      protein - LKTD

<400> SEQUENCE: 25

```
atgaaaatat ggcttagtgg tatttatgaa ttttcctac gctataaaaa catttgggca      60
gaagtatgga aaattcgtaa agaattagac cacccaaaca gaaaaaaaga cgaaagtgaa     120
tttttaccgg cacatttaga actgattgaa accccggttt ctaaaaaacc acgtctaatt     180
gcttatttga ttatgctatt tttagttgtg caattgtgc ttgccagtgt aagcaaagtt      240
gaaattgtgg cgactgctcc cggtaaatta acttttagtg gcagaagtaa agaaattaaa     300
ccgattgaaa acgccattgt acaagaaatt ttcgttaaag atgggcagtt tgtggaaaaa     360
gggcaattat tagtcagctt aactgcattg ggttctgatg cagatatcaa aaagaccatg     420
gcttcacttt ctttagctaa actggagaac tatcgctacc aaactttgct tactgccatt     480
gaaaagagt ccttgccggt gattgattta tctagaaccg aatttaaaga ttcatcggaa      540
gaagatcgac tacgtattaa acacttaatt gaggagcaat acaccacttg caaaaacaa     600
aaaacacaga aaactttagc gtataagcgt aaagaggctg aaaacaaac aatatttgcc     660
tatgtccgta aatatgaagg tgcaacacgt attgaacaag aaaaattaaa agactttaag     720
gcactttata acagaagtc tttatctaag cacgaacttc ttgcgcaaga aaataaatta     780
attgaggctc agaatgagct agctgtttat cgctcaaaat taatgaatt agaaaatgat     840
ctactcaatg taaagaaga acttgaattg atcacgcaat tctttaaaag cgatgtgttg     900
gaaaaattaa agcaacatat tgaaaatgaa cgccaacttc ggctcgagtt agaaaaaaat     960
aatcaacgca gacaggcctc gatgatcaga gcaccggttt ccggtacggt tcagcaactg    1020
aaaattcaca ctataggtgg tgttgttacg actgctgaaa ccttgatgat cattgtgccg    1080
gaagacgatg tgttagaggc caccgctctg gttccaaaca aagatatcgg ctttgttgca    1140
gcagggcagg aggtgattat taaagtggaa actttcccctt atacacgcta tggttatcta    1200
actggtcgaa ttaaacatat tagccccgat gcgattgaac aacctaatgt aggcttagtt    1260
tttaatgcaa ctatagctat agataggaag aatctaacat cgcctgatgg gcgaaaaatt    1320
gatttgagtt caggtatgac aataactgct gaaatcaaaa ccggtgaacg gagtgtaatg    1380
agttatttac tcagcccatt agaagaatct gtcacagaaa gtttaaggga acgc          1434
```

<210> SEQ ID NO 26
<211> LENGTH: 478
<212> TYPE: PRT
<213> ORGANISM: Artificial Sequence
<220> FEATURE:
<223> OTHER INFORMATION: Translation of SEQ ID 25

<400> SEQUENCE: 26

Met Lys Ile Trp Leu Ser Gly Ile Tyr Glu Phe Phe Leu Arg Tyr Lys
1               5                   10                  15

Asn Ile Trp Ala Glu Val Trp Lys Ile Arg Lys Glu Leu Asp His Pro

```
            20                  25                  30
Asn Arg Lys Lys Asp Glu Ser Glu Phe Leu Pro Ala His Leu Glu Leu
            35                  40                  45
Ile Glu Thr Pro Val Ser Lys Lys Pro Arg Leu Ile Ala Tyr Leu Ile
            50                  55                  60
Met Leu Phe Leu Val Val Ala Ile Val Leu Ala Ser Val Ser Lys Val
 65                  70                  75                  80
Glu Ile Val Ala Thr Ala Pro Gly Lys Leu Thr Phe Ser Gly Arg Ser
                    85                  90                  95
Lys Glu Ile Lys Pro Ile Glu Asn Ala Ile Val Gln Glu Ile Phe Val
                100                 105                 110
Lys Asp Gly Gln Phe Val Glu Lys Gly Gln Leu Leu Val Ser Leu Thr
                115                 120                 125
Ala Leu Gly Ser Asp Ala Asp Ile Lys Lys Thr Met Ala Ser Leu Ser
                130                 135                 140
Leu Ala Lys Leu Glu Asn Tyr Arg Tyr Gln Thr Leu Leu Thr Ala Ile
145                 150                 155                 160
Glu Lys Glu Ser Leu Pro Val Ile Asp Leu Ser Arg Thr Glu Phe Lys
                165                 170                 175
Asp Ser Ser Glu Glu Asp Arg Leu Arg Ile Lys His Leu Ile Glu Glu
                180                 185                 190
Gln Tyr Thr Thr Trp Gln Lys Gln Lys Thr Gln Lys Thr Leu Ala Tyr
                195                 200                 205
Lys Arg Lys Glu Ala Glu Lys Gln Thr Ile Phe Ala Tyr Val Arg Lys
                210                 215                 220
Tyr Glu Gly Ala Thr Arg Ile Glu Gln Glu Lys Leu Lys Asp Phe Lys
225                 230                 235                 240
Ala Leu Tyr Lys Gln Lys Ser Leu Ser Lys His Glu Leu Leu Ala Gln
                245                 250                 255
Glu Asn Lys Leu Ile Glu Ala Gln Asn Glu Leu Ala Val Tyr Arg Ser
                260                 265                 270
Lys Leu Asn Glu Leu Glu Asn Asp Leu Leu Asn Val Lys Glu Glu Leu
                275                 280                 285
Glu Leu Ile Thr Gln Phe Phe Lys Ser Asp Val Leu Glu Lys Leu Lys
                290                 295                 300
Gln His Ile Glu Asn Glu Arg Gln Leu Arg Leu Glu Leu Glu Lys Asn
305                 310                 315                 320
Asn Gln Arg Arg Gln Ala Ser Met Ile Arg Ala Pro Val Ser Gly Thr
                325                 330                 335
Val Gln Gln Leu Lys Ile His Thr Ile Gly Gly Val Val Thr Thr Ala
                340                 345                 350
Glu Thr Leu Met Ile Ile Val Pro Glu Asp Asp Val Leu Glu Ala Thr
                355                 360                 365
Ala Leu Val Pro Asn Lys Asp Ile Gly Phe Val Ala Ala Gly Gln Glu
                370                 375                 380
Val Ile Ile Lys Val Glu Thr Phe Pro Tyr Thr Arg Tyr Gly Tyr Leu
385                 390                 395                 400
Thr Gly Arg Ile Lys His Ile Ser Pro Asp Ala Ile Glu Gln Pro Asn
                405                 410                 415
Val Gly Leu Val Phe Asn Ala Thr Ile Ala Ile Asp Arg Lys Asn Leu
                420                 425                 430
Thr Ser Pro Asp Gly Arg Lys Ile Asp Leu Ser Ser Gly Met Thr Ile
                435                 440                 445
```

```
Thr Ala Glu Ile Lys Thr Gly Glu Arg Ser Val Met Ser Tyr Leu Leu
    450                 455                 460

Ser Pro Leu Glu Glu Ser Val Thr Glu Ser Leu Arg Glu Arg
465                 470                 475
```

ATTENUATED *MANNHEIMIA HAEMOLYTICA* VACCINES AND METHODS OF MAKING AND USE

INCORPORATION BY REFERENCE

This application is a Continuation of, and claims benefit of, U.S. patent application Ser. No. Continuation of 14/991,003, filed Jan. 8, 2016, now Granted as U.S. Pat. No. 9,675,682, which is a Divisional of, and claims benefit of, U.S. patent application Ser. No. 14/075,169, filed Nov. 8, 2013, now Granted as U.S. Pat. No. 9,370,561, which claims priority to US provisional patent application Ser. No. USSN 61/723,979, filed on Nov. 8, 2012, and herein incorporated by reference in its entirety.

FIELD OF THE INVENTION

The present invention relates generally to attenuated bacterial vaccines, particularly those providing broad, safe, and effective protection to production animals against infections/disease caused by gram-negative bacteria, including *Mannheimia (Pasteurella) haemolytica*. The invention further relates to methods of producing the attenuated bacteria, and to PCR methods for differentiating among *M. haemolitica* serotypes A1 and A6, in vivo.

The invention accordingly relates to immunogenic or vaccine compositions comprising the bacteria of the invention; e.g., live attenuated bacteria. The bacteria also could be inactivated in the compositions, but it may be advantageous that the bacteria are live attenuated *M. haemolytica* bacteria, either alone, or combined with other bacteria such as *Haemophilus somnus* and/or *Pasteurella multocida*. The invention therefore further relates to methods for preparing and/or formulating such compositions; e.g., culturing or growing or propagating the bacteria on or in suitable medium, harvesting the bacteria, optionally inactivating the bacteria, and optionally admixing the bacteria with a suitable veterinarily or pharmaceutically acceptable carrier, excipient, diluent or vehicle and/or an adjuvant and/or stabilizer. Thus, the invention also relates to the use of the bacteria in formulating such compositions.

BACKGROUND OF THE INVENTION

*M. haemolytica* is a gram negative bacterium normally found in the upper respiratory tract of healthy cattle, sheep and wild sheep. *M. haemolytica* descends into the lungs when cattle experience stress such as shipping, weaning, overcrowding, or viral infections and causes fibrinous and necrotizing bronchopneumonia, a chief component of the bovine respiratory disease complex (BRDC). Economic losses due to BRDC in North America is >$1 billion annually (Bowland and Shewen, 2000). *M. haemolytica* is the bacterium most commonly isolated from the lungs of cattle affected with BRDC. *M. haemolytica* serotype A1 is responsible for approximately 60% of shipping fever, whereas serotypes A6 and A2 account for 26% and 7% respectively (Al-Ghamdi et al., 2000; Purdy et al., 1997). Both *M. haemolytica* A1 and A6 account for >85% of BRDC cases involving bacterial pathogens.

The vaccines currently available in the market against *M. haemolytica* infections are only moderately protective against shipping fever of beef cattle but generally ineffective against neonatal dairy calf pneumonia (Virtala et al., 1996; Rice et al., 2007). The major cause of severe bacterial pneumonia in feedlot and neonatal dairy cattle is *M. haemolytica* serotype A1 followed by serotype A6 (Schreuer et al., 2000, Rice et al., 2007).

Experimental evaluation of all the commercial *M. haemolytica* A1 vaccines used in feedlot showed only partial protection in 50% of the studies (Perino and Hunsaker, 1997). Furthermore, cross-protection against *M. haemolytica* serotypes (either A6 or A2) has been difficult to achieve using conventional vaccine preparations (Purdy et al., 1993; Sabri et al., 2000). Therefore, an efficacious vaccine against *M. haemolytica* serotypes A1 and A6 could significantly improve dairy/beef production.

Effective immunity against *M. haemolytica* is multifaceted. Neutralizing Antibodies against exotoxin leukotoxin A (LktA) and surface antigens are necessary for protective immunity against *M. haemolytica* (Shewen and Wilkie, 1988). Due to the complex genetic machinery involved in controlling the expression of various *M. haemolytica* virulence factors, the specific surface antigens that are important in stimulating immunity have not been clearly determined (Lawrence et al, 2010). However, *M. haemolytica* outer membrane proteins (OMPs) have been implicated in stimulating immunity against surface antigens (Confer et al., 2003, Morton et al., 1995; Potter et al., 1999).

Intranasal immunization of cattle has been pursued for a while using bovine herpesvirus-1 (BoHV-1), bovine respiratory syncytial virus (BRSV) and infectious bovine rhinotracheitis virus (IBR) (Ellis et al., 2007; Muylkens et al., 2007). Commercially available Pfizer's INFORCE 3 when administered intranasally claims to prevent BRSV and also aids in the prevention of respiratory disease caused by IBR and bovine parainfluenza virus type 3 (PI3).

In an experimental study when a modified live leukotoxin deficient *M. haemolytica* mutant was administered intranasally in weaned beef feedlot calves, it resulted in reduced nasopharyngeal colonization with wild type *M. haemolytica* compared to non-vaccinated control calves (Frank et al., 2003). Although intranasal vaccination and leukotoxin deficient *M. haemolytica* are known, inventors are aware of no *M. haemolytica* vaccines successfully combining these concepts.

SUMMARY OF THE INVENTION

An object of the present disclosure is to provide effective vaccines comprising attenuated *M. haemolytica* serotypes A1 & A6. Relative to a parent *M. haemolytica* serotype A1 or A6 strain, the attenuated strains may have genomic modifications, including deletions, substitutions, and additions, and whose presence (or absence) is associated with reduced virulence. In an embodiment, a wildtype *M. haemolytica* (serotype A1 D153) may be modified to contain a partial gene deletion of the leukotoxin CA (lktCA) genomic locus, resulting in an attenuated bacterium, which secretes a truncated, noncytotoxic form of LktA protein. The vaccines ideally provide safe, effective, and broad protective immunity.

Another object of the disclosure is to provide multi-valent vaccines, comprising the attenuated *M. haemolytica* in combination with other bacteria, including *P. multocida, M. haemolytica* serotype A6, and *Histophilus somni* (*H. somni*). Thus, the invention encompasses a 4-way avirulent, modified live vaccine useful against bovine respiratory disease.

A further object of this invention is to provide methods for treatment and prophylaxis of infection bovine respiratory disease, comprising the steps of administering effective amounts of the inventive vaccines to susceptible bovine animals.

In one embodiment, the attenuated vaccines further comprises an adjuvant. The adjuvant may be any substance which increases and/or augments the elicited immune response, as compared to attenuated vaccine alone. Mucosal adjuvants, including chitosans and derivatives thereof, are particularly useful for the disclosed oral attenuated vaccines.

The invention further provides methods for inducing an immunological (or immunogenic) or protective response against *M. haemolytica*, as well as methods for preventing or treating *M. haemolytica*, or disease state(s) caused by *M. haemolytica*, comprising administering the attenuated bacteria, or a composition comprising the attenuated bacteria to animals in need thereof.

In addition, the disclosure provides PCR methods and reagents useful for diagnosing and/or discriminating between *M. haemolytica* serotypes A1 and A6. Comparative genomic sequence analysis, further described below, revealed A1- and A6-specific genes, which provide the basis for the methods and reagents provided in this disclosure.

Kits comprising at least the attenuated *M. haemolytica* strain and instructions for use are also provided.

These and other embodiments are disclosed or are obvious from and encompassed by, the following Detailed Description.

BRIEF DESCRIPTION OF THE DRAWINGS

A full and enabling disclosure of the present invention, including the best mode thereof, to one of ordinary skill in the art, is set forth more particularly in the remainder of the specification, including reference to the accompanying figures, wherein:

FIG. 1 presents the scheme used to produce the pCT109GA189ΔlktCA-Kan plasmid (replacement plasmid). The final product for vaccine manufacture incorporated a consensus ribosome-binding site (AGGAGG, rbs) upstream of the start codon which replaced the poor lktC rbs and increased expression of leukotoxoid. The native lktA gene, deleted in the vaccine strain, uses a strong rbs (AGGAGA). For this product, lktRBSr primer was used in-lieu of lktCAdelr primer. The consensus site is underlined;

FIG. 2 illustrates integration of the replacement plasmid into the bacterial genome;

FIG. 3 depicts resolution/excision of the replacement plasmid, leaving behind only the desired ΔlktCA sequence, stably integrated into the bacterial genome, and encoding the truncated LktA protein;

FIG. 4A agarose gel electrophoresis of PCR products from *M. haemolytica* LktCABD operon showing truncated LktCA (lane 2) and wildtype LktCA (lane 3);

FIG. 4B Western blot analysis of truncated LktA expressed by *M. haemolytica* D153Δ-1-PKL, vaccine strain. Lanes: 1—marker; 2—5 μl of culture supernatant containing truncated LktA (*=27 kDa, *M. haemolytica* D153Δ-1-PKL); 3—5 μl of culture supernatant containing wildtype LktA (*=102 kDa, *M. haemolytica* D153 parent strain);

FIG. 5 is a Venn diagram representing the unique and overlapping genes present in five *M. haemolytica* isolates.

DETAILED DESCRIPTION OF THE INVENTION

The present invention relates to a *M. haemolytica* vaccine or composition which may comprise an attenuated *M. haemolytica* strain and a pharmaceutically or veterinarily acceptable carrier, excipient, or vehicle, which elicits, induces or stimulates a response in an animal.

In order to develop an effective *M. haemolytica* intranasal vaccine, which protects bovines against serogroups A1/A6, inventors used *M. haemolytica* having a partially deleted LktA gene. This bacterium does not cause cytolysis, but is able to elicit neutralizing antibodies. Prior to the instant disclosure, it was not known whether intranasal administration (or administration via any route) would elicit in bovines a protective immune response.

Although there are serological methods to distinguish *M. haemolytica* A1 and A6 these methods are not always reliable and developing strong antisera against A6 is particularly difficult. To overcome this problem, inventors sequenced both A1 and A6 genomes, performed a comparative genomic analysis and developed a real time quantitative polymerase chain reaction (RT-QPCR) method to distinguish between A1 and A6 field isolates and to track our intranasal vaccine combination (*M. haemolytica, M. somnus*, and *P. multocida*).

Thus, an embodiment of this disclosure provides useful RT-QPCR methods, which enable at least the following activities: a) identification of field isolates of *M. haemolytica* A1 and A6 quickly and screen large number of colonies; b) monitoring of vaccination/colonization of A1 and A6 in nasal cavities; c) elimination of the need for developing high titer antisera; and d) development of rapid, automated diagnostic test kits.

The present invention further provides attenuated *M. haemolytica* strains having a deletion in at least one virulence gene. In an embodiment, the deletion is within LktCA, a locus that encodes an enzyme acylase (LktC) and leukotoxin A (LktA), the chief cytotoxin. This deletion may be amplified by polymerase chain reaction (PCR) and the secretion of a truncated LktA can be detected on a Western blot to determine if the bacterium is the mutant or wildtype.

Deletion of genomic sequence(s) from virulent parental bacteria to produce avirulent, attenuated mutant bacteria is accomplished through novel and non-obvious inventive activity. Such mutant bacteria, also referred to herein as modified-live microorganisms (MLM) are useful for the production of immunogenic compositions or vaccines having both a high degree of immunogenicity and a low (to non-existent) degree of pathogenicity.

These mutants are also useful as vectors which can be useful for expression in vitro of expression products, as well as for reproduction or replication of nucleotide sequences (e.g., replication of DNA), and for in vivo expression products.

Engineering of the deletion mutations provides novel and nonobvious nucleotide sequences and genes, as well as novel and nonobvious gene products encoded by the nucleotide sequences and genes. Such gene products provide antigens, immunogens and epitopes, and are useful as isolated gene products. Such isolated gene products, as well as epitopes thereof, are also useful for generating antibodies, which are useful in diagnostic applications.

Such gene products, which can provide or generate epitopes, antigens or immunogens, are also useful for immunogenic or immunological compositions, as well as vaccines.

In an aspect, the invention provides bacteria containing an attenuating mutation in a nucleotide sequence or a gene wherein the mutation modifies, reduces or abolishes the expression and/or the biological activity of a polypeptide or protein encoded by a gene, resulting in attenuated virulence of the bacterium. In a particular embodiment, the mutation is an in-frame deletion resulting in the bacterium secreting a truncated leukotoxin. In a particular embodiment, the truncated leukotoxin migrates at about 27 kD on a typical SDS gel.

Attenuation reduces or abolishes the pathogenicity of the bacteria and the gravity of the clinical signs or lesions, decreases the growth rate of the bacteria, and prevents the death from the bacteria.

In particular, the present invention encompasses attenuated *M. haemolytica* strains and vaccines comprising the same, which elicit an immunogenic response in an animal, particularly the attenuated *M. haemolytica* strains that elicit, induce or stimulate a response in a bovine.

Particular *M. haemolytica* attenuated strains of interest have mutations in genes, relative to wild type virulent parent strain, which are associated with virulence. It is recognized that, in addition to strains having the disclosed mutations, attenuated strains having any number of mutations in the disclosed virulence genes can be used in the practice of this invention.

In another aspect, the novel attenuated *M. haemolytica* strains are formulated into safe, effective vaccine against *M. haemolytica* and infections/diseases cause by *M. haemolytica*.

In an embodiment, the *M. haemolytica* vaccines further comprise an adjuvant. In a particular embodiment, the adjuvant is a mucosal adjuvant, such as chitosan, methylated chitosan, trimethylated chitosan, or derivatives or combinations thereof.

As defined herein, the term "gene" will be used in a broad sense, and shall encompass both coding and non-coding sequences (i.e. upstream and downstream regulatory sequences, promoters, 5'/3' UTR, introns, and exons). Where reference to only a gene's coding sequence is intended, the term "gene's coding sequence" or "CDS" will be used interchangeably throughout this disclosure.

By "antigen" or "immunogen" means a substance that induces a specific immune response in a host animal. The antigen may comprise a whole organism, killed, attenuated or live; a subunit or portion of an organism; a recombinant vector containing an insert with immunogenic properties; a piece or fragment of DNA capable of inducing an immune response upon presentation to a host animal; a polypeptide, an epitope, a hapten, or any combination thereof. Alternately, the immunogen or antigen may comprise a toxin or antitoxin.

The terms "protein", "peptide", "polypeptide" and "polypeptide fragment" are used interchangeably herein to refer to polymers of amino acid residues of any length. The polymer can be linear or branched, it may comprise modified amino acids or amino acid analogs, and it may be interrupted by chemical moieties other than amino acids. The terms also encompass an amino acid polymer that has been modified naturally or by intervention; for example disulfide bond formation, glycosylation, lipidation, acetylation, phosphorylation, or any other manipulation or modification, such as conjugation with a labeling or bioactive component.

The term "immunogenic or antigenic polypeptide" as used herein includes polypeptides that are immunologically active in the sense that once administered to the host, it is able to evoke an immune response of the humoral and/or cellular type directed against the protein. Preferably the protein fragment is such that it has substantially the same immunological activity as the total protein. Thus, a protein fragment according to the invention comprises or consists essentially of or consists of at least one epitope or antigenic determinant. An "immunogenic" protein or polypeptide, as used herein, includes the full-length sequence of the protein, analogs thereof, or immunogenic fragments thereof. By "immunogenic fragment" is meant a fragment of a protein which includes one or more epitopes and thus elicits the immunological response described above. Such fragments can be identified using any number of epitope mapping techniques, well known in the art. See, e.g., Epitope Mapping Protocols in Methods in Molecular Biology, Vol. 66 (Glenn E. Morris, Ed., 1996). For example, linear epitopes may be determined by e.g., concurrently synthesizing large numbers of peptides on solid supports, the peptides corresponding to portions of the protein molecule, and reacting the peptides with antibodies while the peptides are still attached to the supports. Such techniques are known in the art and described in, e.g., U.S. Pat. No. 4,708,871; Geysen et al., 1984; Geysen et al., 1986. Similarly, conformational epitopes are readily identified by determining spatial conformation of amino acids such as by, e.g., x-ray crystallography and 2-dimensional nuclear magnetic resonance. See, e.g., Epitope Mapping Protocols, supra. Methods especially applicable to the proteins of *T. parva* are fully described in PCT/US2004/022605 incorporated herein by reference in its entirety.

As discussed herein, the invention encompasses active fragments and variants of the antigenic polypeptide. Thus, the term "immunogenic or antigenic polypeptide" further contemplates deletions, additions and substitutions to the sequence, so long as the polypeptide functions to produce an immunological response as defined herein. The term "conservative variation" denotes the replacement of an amino acid residue by another biologically similar residue, or the replacement of a nucleotide in a nucleic acid sequence such that the encoded amino acid residue does not change or is another biologically similar residue. In this regard, particularly preferred substitutions will generally be conservative in nature, i.e., those substitutions that take place within a family of amino acids. For example, amino acids are generally divided into four families: (1) acidic—aspartate and glutamate; (2) basic—lysine, arginine, histidine; (3) non-polar—alanine, valine, leucine, isoleucine, proline, phenylalanine, methionine, tryptophan; and (4) uncharged polar—glycine, asparagine, glutamine, cystine, serine, threonine, tyrosine. Phenylalanine, tryptophan, and tyrosine are sometimes classified as aromatic amino acids. Examples of conservative variations include the substitution of one hydrophobic residue such as isoleucine, valine, leucine or methionine for another hydrophobic residue, or the substitution of one polar residue for another polar residue, such as the substitution of arginine for lysine, glutamic acid for aspartic acid, or glutamine for asparagine, and the like; or a similar conservative replacement of an amino acid with a structurally related amino acid that will not have a major effect on the biological activity. Proteins having substantially the same amino acid sequence as the reference molecule but possessing minor amino acid substitutions that do not substantially affect the immunogenicity of the protein are, therefore, within the definition of the reference polypeptide. All of the polypeptides produced by these modifications are included herein. The term "conservative variation" also includes the use of a substituted amino acid in place of an unsubstituted parent amino acid provided that antibodies raised to the substituted polypeptide also immunoreact with the unsubstituted polypeptide.

The term "epitope" refers to the site on an antigen or hapten to which specific B cells and/or T cells respond. The term is also used interchangeably with "antigenic determinant" or "antigenic determinant site". Antibodies that recognize the same epitope can be identified in a simple immunoassay showing the ability of one antibody to block the binding of another antibody to a target antigen.

An "immunological response" to a composition or vaccine is the development in the host of a cellular and/or antibody-mediated immune response to a composition or vaccine of interest. Usually, an "immunological response" includes but is not limited to one or more of the following effects: the production of antibodies, B cells, helper T cells, and/or cytotoxic T cells, directed specifically to an antigen or antigens included in the composition or vaccine of interest. Preferably, the host will display either a therapeutic or protective immunological response such that resistance to new infection will be enhanced and/or the clinical severity of the disease reduced. Such protection will be demonstrated by either a reduction or lack of symptoms and/or clinical disease signs normally displayed by an infected host, a quicker recovery time and/or a lowered viral titer in the infected host.

By "animal" is intended mammals, birds, and the like. Animal or host as used herein includes mammals and human. The animal may be selected from the group consisting of equine (e.g., horse), canine (e.g., dogs, wolves, foxes, coyotes, jackals), feline (e.g., lions, tigers, domestic cats, wild cats, other big cats, and other felines including cheetahs and lynx), ovine (e.g., sheep), bovine (e.g., cattle), porcine (e.g., pig), avian (e.g., chicken, duck, goose, turkey, quail, pheasant, parrot, finches, hawk, crow, ostrich, emu and cassowary), primate (e.g., prosimian, tarsier, monkey, gibbon, ape), ferrets, seals, and fish. The term "animal" also includes an individual animal in all stages of development, including newborn, embryonic and fetal stages.

Unless otherwise explained, all technical and scientific terms used herein have the same meaning as commonly understood by one of ordinary skill in the art to which this disclosure belongs. The singular terms "a", "an", and "the" include plural referents unless context clearly indicates otherwise. Similarly, the word "or" is intended to include "and" unless the context clearly indicate otherwise.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

The term "nucleic acid" and "polynucleotide" refers to RNA or DNA that is linear or branched, single or double stranded, or a hybrid thereof. The term also encompasses RNA/DNA hybrids. The following are non-limiting examples of polynucleotides: a gene or gene fragment, exons, introns, mRNA, tRNA, rRNA, ribozymes, cDNA, recombinant polynucleotides, branched polynucleotides, plasmids, vectors, isolated DNA of any sequence, isolated RNA of any sequence, nucleic acid probes and primers. A polynucleotide may comprise modified nucleotides, such as methylated nucleotides and nucleotide analogs, uracyl, other sugars and linking groups such as fluororibose and thiolate, and nucleotide branches. The sequence of nucleotides may be further modified after polymerization, such as by conjugation, with a labeling component. Other types of modifications included in this definition are caps, substitution of one or more of the naturally occurring nucleotides with an analog, and introduction of means for attaching the polynucleotide to proteins, metal ions, labeling components, other polynucleotides or solid support. The polynucleotides can be obtained by chemical synthesis or derived from a microorganism.

The term "gene" is used broadly to refer to any segment of polynucleotide associated with a biological function. Thus, genes include introns and exons as in genomic sequence, or just the coding sequences as in cDNAs and/or the regulatory sequences required for their expression. For example, gene also refers to a nucleic acid fragment that expresses mRNA or functional RNA, or encodes a specific protein, and which includes regulatory sequences.

An "isolated" biological component (such as a nucleic acid or protein or organelle) refers to a component that has been substantially separated or purified away from other biological components in the cell of the organism in which the component naturally occurs, for instance, other chromosomal and extra-chromosomal DNA and RNA, proteins, and organelles. Nucleic acids and proteins that have been "isolated" include nucleic acids and proteins purified by standard purification methods. The term also embraces nucleic acids and proteins prepared by recombinant technology as well as chemical synthesis.

The term "conservative variation" denotes the replacement of an amino acid residue by another biologically similar residue, or the replacement of a nucleotide in a nucleic acid sequence such that the encoded amino acid residue does not change or is another biologically similar residue. In this regard, particularly preferred substitutions will generally be conservative in nature, as described above.

The term "recombinant" means a polynucleotide with semisynthetic, or synthetic origin which either does not occur in nature or is linked to another polynucleotide in an arrangement not found in nature.

"Heterologous" means derived from a genetically distinct entity from the rest of the entity to which it is being compared. For example, a polynucleotide may be placed by genetic engineering techniques into a plasmid or vector derived from a different source, and is a heterologous polynucleotide. A promoter removed from its native coding sequence and operatively linked to a coding sequence other than the native sequence is a heterologous promoter.

The polynucleotides of the invention may comprise additional sequences, such as additional encoding sequences within the same transcription unit, controlling elements such as promoters, ribosome binding sites, 5'UTR, 3'UTR, transcription terminators, polyadenylation sites, additional transcription units under control of the same or a different promoter, sequences that permit cloning, expression, homologous recombination, and transformation of a host cell, and any such construct as may be desirable to provide embodiments of this invention.

Methods of Use and Article of Manufacture

The present invention includes the following method embodiments. In an embodiment, a method of vaccinating an animal comprising administering a composition comprising an attenuated *M. haemolytica* strain and a pharmaceutical or veterinarily acceptable carrier, excipient, or vehicle to an animal is disclosed. In one aspect of this embodiment, the animal is a bovine.

The dose volume of compositions for target species that are mammals, e.g., the dose volume of pig or swine compositions, based on bacterial antigens, is generally between about 0.1 to about 2.0 ml, between about 0.1 to about 1.0 ml, and between about 0.5 ml to about 1.0 ml.

The efficacy of the vaccines may be tested about 2 to 4 weeks after the last immunization by challenging animals, such as bovine, with a virulent strain of *M. haemolytica*. Both homologous and heterologous strains are used for challenge to test the efficacy of the vaccine. The animal may be challenged by IM or SC injection, spray, intra-nasally, intra-ocularly, intra-tracheally, and/or orally. Samples from joints, lungs, brain, and/or mouth may be collected before and post-challenge and may be analyzed for the presence of *M. haemolytica*-specific antibody.

The compositions comprising the attenuated bacterial strains of the invention used in the prime-boost protocols are contained in a pharmaceutically or veterinary acceptable vehicle, diluent or excipient. The protocols of the invention protect the animal from *M. haemolytica* and/or prevent disease progression in an infected animal.

The various administrations are preferably carried out 1 to 6 weeks apart. Preferred time interval is 3 to 5 weeks, and optimally 4 weeks according to one embodiment, an annual booster is also envisioned. The animals, for example pigs, may be at least 3-4 weeks of age at the time of the first administration.

It should be understood by one of skill in the art that the disclosure herein is provided by way of example and the present invention is not limited thereto. From the disclosure herein and the knowledge in the art, the skilled artisan can determine the number of administrations, the administration route, and the doses to be used for each injection protocol, without any undue experimentation.

Another embodiment of the invention is a kit for performing a method of eliciting or inducing an immunological or protective response against *M. haemolytica* in an animal comprising an attenuated *M. haemolytica* immunological composition or vaccine and instructions for performing the method of delivery in an effective amount for eliciting an immune response in the animal.

Another embodiment of the invention is a kit for performing a method of inducing an immunological or protective response against *M. haemolytica* in an animal comprising a composition or vaccine comprising an attenuated *M. haemolytica* strain of the invention, and instructions for performing the method of delivery in an effective amount for eliciting an immune response in the animal.

Yet another aspect of the present invention relates to a kit for prime-boost vaccination according to the present invention as described above. The kit may comprise at least two vials: a first vial containing a vaccine or composition for the prime-vaccination according to the present invention, and a second vial containing a vaccine or composition for the boost-vaccination according to the present invention. The kit may advantageously contain additional first or second vials for additional prime-vaccinations or additional boost-vaccinations.

The pharmaceutically or veterinarily acceptable carriers or vehicles or excipients are well known to the one skilled in the art. For example, a pharmaceutically or veterinarily acceptable carrier or vehicle or excipient can be a 0.9% NaCl (e.g., saline) solution or a phosphate buffer. Other pharmaceutically or veterinarily acceptable carrier or vehicle or excipients that can be used for methods of this invention include, but are not limited to, poly-(L-glutamate) or polyvinylpyrrolidone. The pharmaceutically or veterinarily acceptable carrier or vehicle or excipients may be any compound or combination of compounds facilitating the administration of the vector (or protein expressed from an inventive vector in vitro); advantageously, the carrier, vehicle or excipient may facilitate transfection and/or improve preservation of the vector (or protein). Doses and dose volumes are herein discussed in the general description and can also be determined by the skilled artisan from this disclosure read in conjunction with the knowledge in the art, without any undue experimentation.

The immunological compositions and vaccines according to the invention may comprise or consist essentially of one or more adjuvants. Suitable adjuvants for use in the practice of the present invention are (1) polymers of acrylic or methacrylic acid, maleic anhydride and alkenyl derivative polymers, (2) immunostimulating sequences (ISS), such as oligodeoxyribonucleotide sequences having one or more non-methylated CpG units (Klinman et al., 1996; WO98/16247), (3) an oil in water emulsion, such as the SPT emulsion described on page 147 of "Vaccine Design, The Subunit and Adjuvant Approach" published by M. Powell, M. Newman, Plenum Press 1995, and the emulsion MF59 described on page 183 of the same work, (4) cationic lipids containing a quaternary ammonium salt, e.g., DDA (5) cytokines, (6) aluminum hydroxide or aluminum phosphate, (7) saponin or (8) other adjuvants discussed in any document cited and incorporated by reference into the instant application, or (9) any combinations or mixtures thereof.

In an embodiment, adjuvants include those which promote improved absorption through mucosal linings. Some examples include MPL, LTK63, toxins, PLG microparticles and several others (Vajdy, M. Immunology and Cell Biology (2004) 82, 617-627). In an embodiment, the adjuvant may be a chitosan (Van der Lubben et al. 2001; Patel et al. 2005; Majithiya et al. 2008; U.S. Pat. No. 5,980,912).

In an embodiment, the adjuvant may be inactivated bacteria, an inactivated virus, fractions of inactivated bacteria, bacterial lipopolysaccharides, bacterial toxins, or derivatives or References.

Ackermann, M. R, Brogden, K. A. 2000. Response of the ruminant respiratory tract to *Mannheimia (Pasteurella) haemolytica*. Microbes Infect. 2:1079-1088.

Al-Ghamdi, G. M., et al, 2000. Serotyping of *Mannheimia (Pasteurella) haemolytica* isolates from the upper Midwest United States. J. Vet. Diagn. Invest. 12, 576-578.

Bowland, S., Shewen, P., 2000. Bovine respiratory disease: commercial vaccines currently available in Canda. Can. Vet. J. 41, 33-38.

Briggs R. E, Tatum F. M. 2005. Generation and molecular characterization of new temperature-sensitive plasmids intended for genetic engineering of Pasteurellaceae. Appl Environ Micobiol 71:7187-7195.

Burriel, A. R. 1997. News & Notes: Isolation of *Pasteurella haemolytica* from Grass, Drinking Water, and Straw Bedding Used by Sheep. Curr. Microbiol. 35: 316-318.

Confer, A. W., et al., 2003. Immunogenicity of recombinant Mannheimia haemolytica serotype 1 outer membrane protein PlpE and augmentation of a commercial vaccine. Vaccine 21, 2821-2829.

Davies, R. L, et al. 2002. Mosaic structure and molecular evolution of the leukotoxin operon (lktCABD) in *Mannheimia (Pasteurella) haemolytica, Mannheimia glucosida*, and *Pasteurella trehalosi*. J Bacteriol. 184(1):266-277.

Davies, R. L, et al. 2001. Sequence diversity and molecular evolution of the leukotoxin (lktA) gene in bovine and ovine strains of *Mannheimia (Pasteurella) haemolytica*. J Bacteriol. 183(4):1394-1404.

Ellis, J., et al., 2007. Response of calves to challenge exposure with virulent bovine respiratory syncytial virus following intranasal administration of vaccines formulated for parenteral administration. J. Am. Vet. Med. Assoc. 230, 233-243.

Frank, G. H, et al. 2003. Effect of intranasal exposure to leukotoxin-deficient *Mannheimia haemolytica* at the time of arrival at the feedyard on subsequent isolation of *M. haemolytica* from nasal secretions of calves. Am J Vet Res. 64(5):580-585.

Gioia, J. et al. 2006. The genome sequence of *Mannheimia haemolytica* A1: insights into virulence, natural competence, and Pasteurellaceae phylogeny. J Bacteriol. 188 (20):7257-7266.

Lawrence, P. K., et al., 2010. Three-way comparative genomic analysis of two *Mannheimia haemolytica* isolates. BMC Genomics. 11:535 (Open access).

Morton, R. J., et al., 1995. Vaccination of cattle with outer membrane protein-enriched fractions of *Pasteurella haemolytica* and resistance against experimental challenge exposure. Am. J. Vet. Res. 56, 875-879.

Miller, M. W. 2001. Pasteurellosis, In E. S. Williams and I. K. Barker (ed.), Infectious diseases of wild mammals. Iowa State University. Press, Ames, Iowa p. 330-339

Mosier, D. A. 1997. Bacterial pneumonia. Vet. Clin. N. Am. Food Anim. Pract. 13:483-493.

Muylkens, B., et al., 2007. Bovine herpesvirus 1 infection and infectious bovine rhinotracheitis. Vet. Res. 38, 181-209.

Potter, A. A., et al., 1999. Protective capacity of the *Pasteurella haemolytica* transferrin-binding proteins TbpA and TbpB in cattle. Microb Pathog 27, 197-206.

Perino, L. J., Hunsaker, B. D., 1997. A review of bovine respiratory disease vaccine field efficacy. The Bovine Practitioner 31, 59-66.

Purdy, C. W., et al, 1993. Efficacy of *Pasteurella haemolytica* subunit antigens in a goat model of pasteurellosis. Am. J. Vet. Res. 54, 1637-1647.

Purdy, C. W., et al., 1997. Efficacy of a subcutaneously administered, ultraviolet light-killed *Pasteurella multocida* A:3-containing bacterin against transthoracic challenge exposure in goats. Am. J. Vet. Res. 58, 841-847.

Rehmtulla, A. J, Thomson, R.G. 1981. A review of the lesions in shipping fever of cattle. Can. Vet. J. 22:1

Rice, J. A., et al., 2007. *Mannheimia haemolytica* and bovine respiratory disease. Anim. Health Res. Rev. 8, 117-128.

Sabri, M. Y., et al., 2000. Efficacy of an outer membrane protein of *Pasteurella haemolytica* A2, A7 or A9-enriched vaccine against intratracheal challenge exposure in sheep. Vet. Microbiol. 73, 13-23.

Schreuer, D., et al. 2000. Evaluation of the efficacy of a new combined (*Pasteurella*) *Mannheimia haemolytica* serotype A1 and A6 vaccine in pre-ruminant calves by virulent challenge. Journal Cattle Practice Vol. 8 No. 1 pp. 9-12

Shewen, P. E., Wilkie, B. N., 1988. Vaccination of calves with leukotoxic culture supernatant from *Pasteurella haemolytica*. Can. J. Vet. Res. 52, 30-36.

Virtala, A. M., et al., 1996. Epidemiologic and pathologic characteristics of respiratory tract disease in dairy heifers during the first three months of life. J. Am. Vet. Med. Assoc. 208, 2035-2042.

The invention will now be further described by way of the following non-limiting examples.

EXAMPLES

Example 1

Production of Attenuated *M. Haemolytica*

*M. haemolytica* is a commensal organism of the upper respiratory tract of calves and other ruminants. Under stress and in immunocompromised animals *M. haemolytica* descends into lungs and causes severe systemic disease resulting in pneumonic pasteurellosis or "shipping fever". The pathogen can be spread by nose to nose contact. To attenuate the bacterium, we deleted nucleotides within the LktCA locus, which encodes an enzyme acylase (LktC) and leukotoxin A (LktA), the bacterium's chief cytotoxin. This deletion can be amplified by polymerase chain reaction (PCR) and the secretion of a truncated LktA can be detected on a Western blot to determine if the bacterium is the mutant or wildtype. The genetic engineering is summarized in FIGS. 1-3. All reagents, including the shuttle vectors pCR2.1, pBC SK, pSK, and pCT109GA189 is ori, and the *E. coli* DH11S host cell, are well-known to and accessible by persons skilled in the art.

Figure 1B:
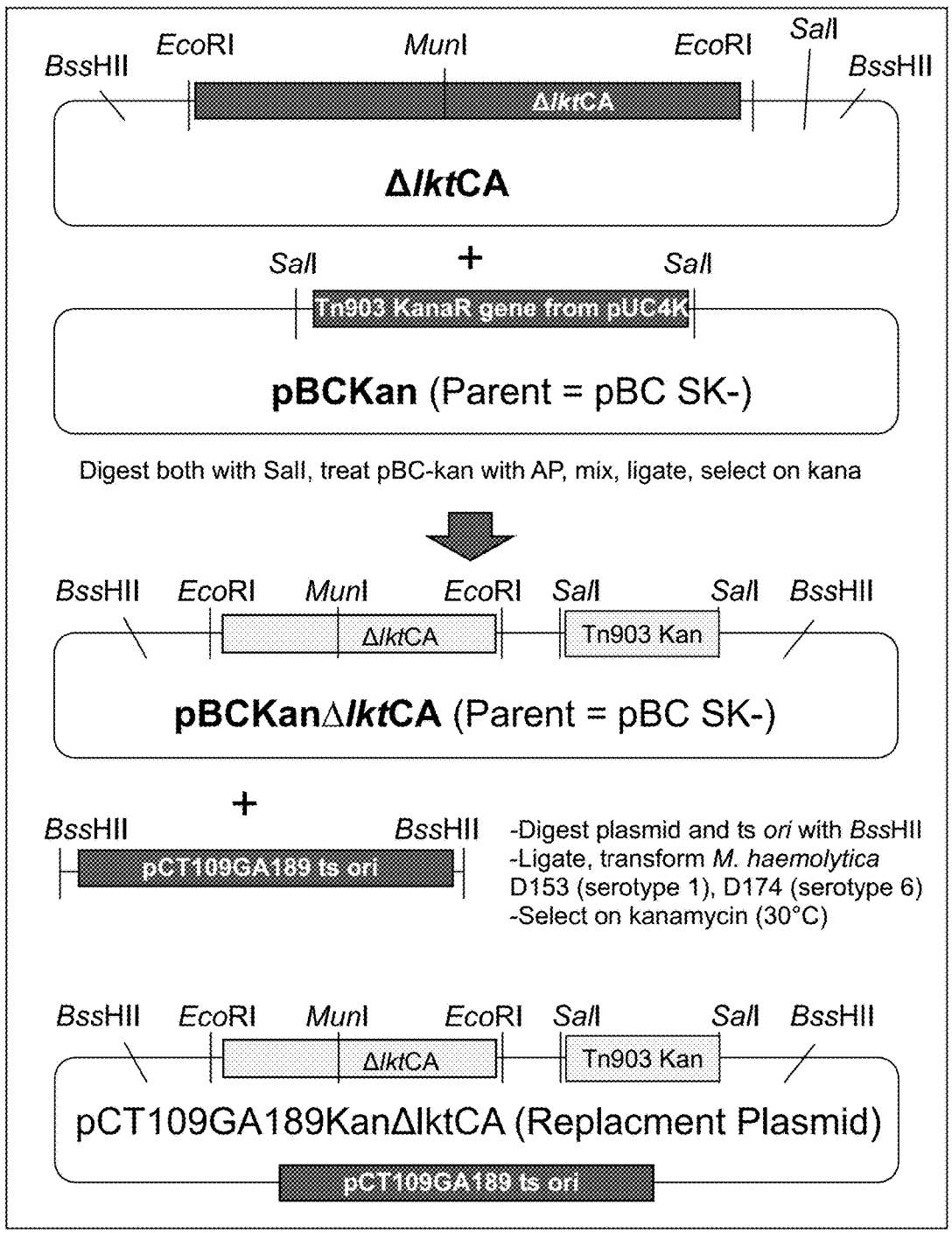
Figure 2:
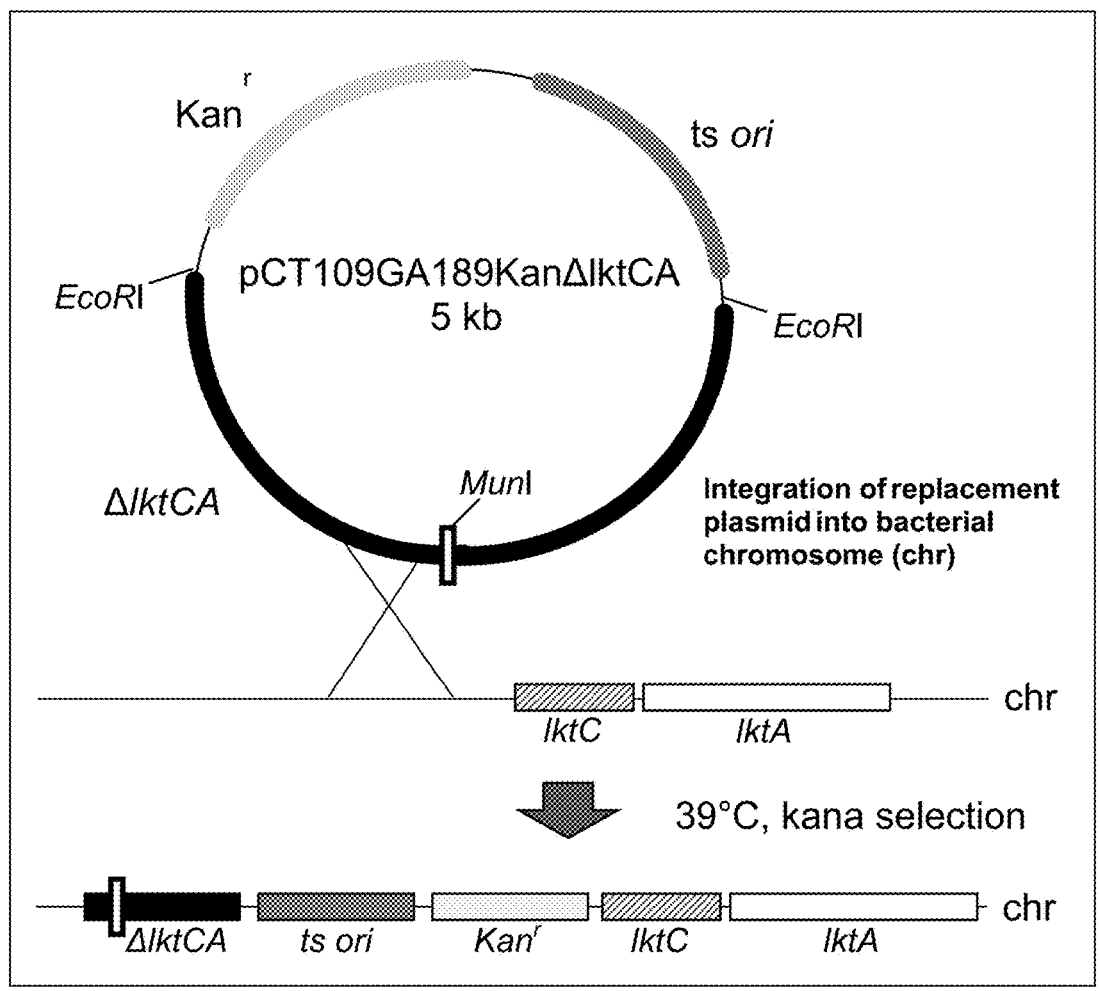
Figure 3:
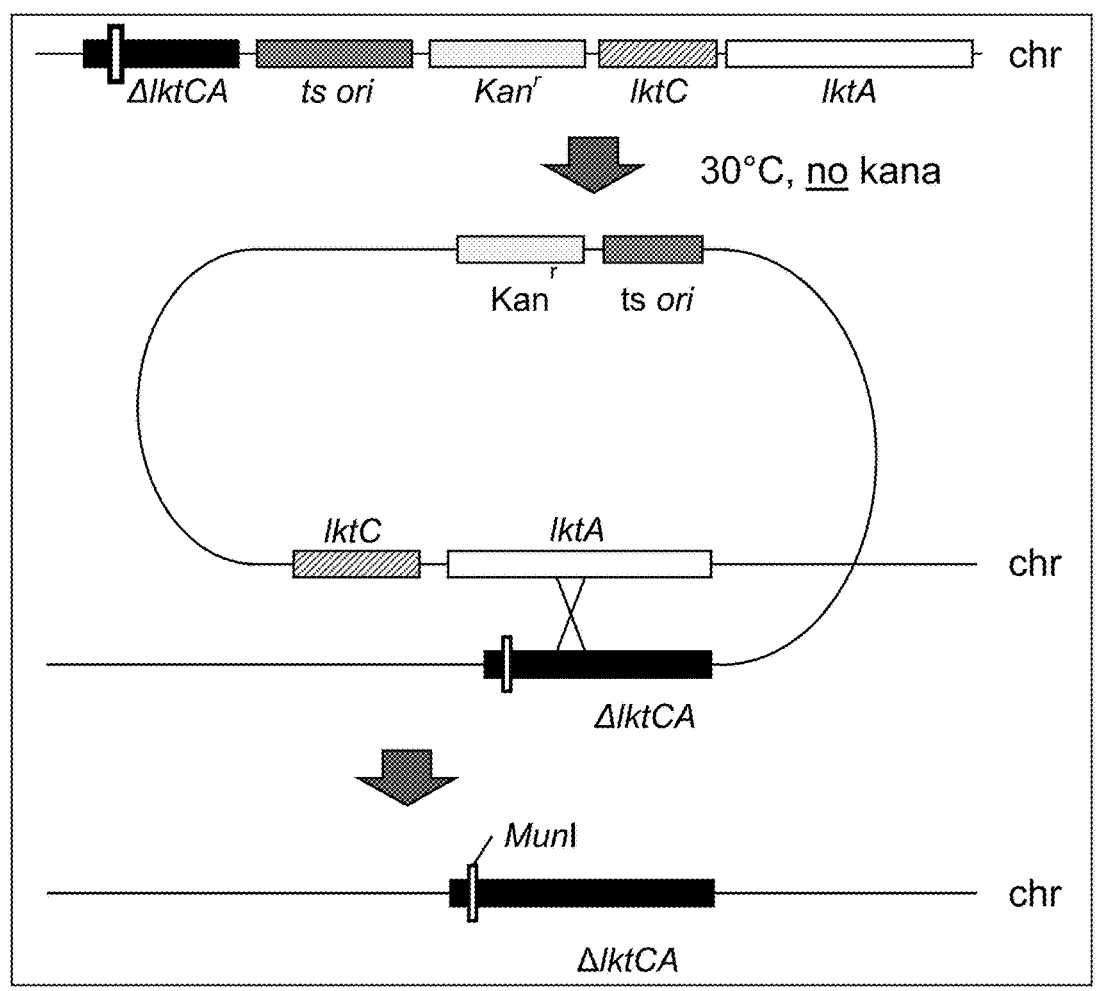

Construction of lktCA deletion. pCT109GA189-KanΔlktCA and pCT109GA189-KanΔlktCA-rbs were constructed as outlined in FIGS. 1-3. Briefly, two DNA fragments, upstream (1.06 kb, SEQ ID NO:6) and downstream (1.29 kb, SEQ ID NO:7) were PCR amplified from *M. haemolytica* strain NADC D153 (FIG. 1). Whole cells were used as template using the primer sets, lktCAf (SEQ ID NO:1)/lktCAdelr (SEQ ID NO:4) and lktCAr (SEQ ID NO:2)/lktCAdelf (SEQ ID NO:3). The PCR products were phenol-chloroform-extracted to inactivate Taq polymerase and then digested with MunI prior to ligation. The ligation products were PCR amplified with primer pair lktCAf/lktCAr and the products were cloned using a commercially available vector (PCR2.1, Invitrogen, Carlsbad, Calif.) according to manufacturer instructions.

A product containing an approximately 2.3 kb insert was selected and proper sequence across the deletion was confirmed by DNA sequencing and designated pTAΔlktCA. A kanamycin cassette derived from pUC4K was placed into the SalI site of pBC SK-(Stratagene Inc.) to generate pBCKan. The 2.3 kb deleted leukotoxin insert in pTAΔlktCA was transferred into pBCKan by digestion with EcoRI and ligation into the unique EcoRI site to form pBCKanΔlktCA. This product was amplified by PCR using primer pair lktCAdelf (SEQ ID NO:3) and lktRBSr (SEQ ID NO:5) to replace the native lktC ribosome binding site (RBS) with a consensus RBS (FIG. 1). The product was digested with MunI and ligated onto itself to form pBCKanΔlktCArbs. Proper sequence adjacent to the deletion was confirmed by DNA sequencing. Finally the pBC plasmid backbone of both pBCKanΔlktCA and pBCKanΔlktCArbs was replaced with the temperature-sensitive plasmid origin of replication from pCT109GA189 (Briggs and Tatum, 2005) by ligating BssHII-digested preparations of each to generate pCT109GA189KanΔlktCA and pCT109GA189KanΔlktCArbs.

Electrocompetent *M. haemolytica* serotype A1 D153 cells (virulent parental strain) were transformed with pCT109GA189KanΔlktCA and pCT109GA189KanΔlktCArbs by previously described methods except unmethylated ligation product was directly introduced into the competent cells. (Briggs and Tatum, 2005) Briefly, cells were made electrocompetent by growing them to logarithmic phase in 100 ml of Columbia broth (Difco Laboratories, Detroit, Mich.) at 37° C. with gentle shaking. The cells were pelleted by centrifugation at 5,000 μg and washed in 100 ml of 272 mM sucrose at 0° C., and the pellet was suspended in an equal volume of 272 mM sucrose at 0° C. After electroporation, cells recovered overnight in 10 ml Columbia broth at 30° C. Growth (50 μl) was spread onto Columbia agar plates containing 50 μg/ml kanamycin, which were then incubated 36 hours at 30° C.

Individual colonies were passed to broth containing 50 μ/ml kanamycin and incubated overnight at 30° C. Growth (100 μl) was passed again to Columbia agar plates with kanamycin which were incubated overnight at 39° C. Individual colonies were passed to trypticase soy agar (TSA) plates containing 5% defibrinated sheep blood (BA plates, incubated overnight at 39° C.) and to Columbia broth without selection (incubated overnight at 30° C.). Growth in broth was streaked for isolation on BA plates and passed again in broth at 30° C. Non-hemolytic colonies which were kanamycin-sensitive were detected on BA plates after 1 to 3 passages without selection. Representative colonies from each recipient strain and replacement plasmid were selected for further study.

Because the temperature-sensitive plasmid origin functions poorly in *E. coli* cloning hosts, these final ligation products were introduced directly into *M. haemolytica*. Prior cloning steps used *E. coli* DH11S (Life Technologies, Rockville, Md.) as the cloning host.

Figure 4A:
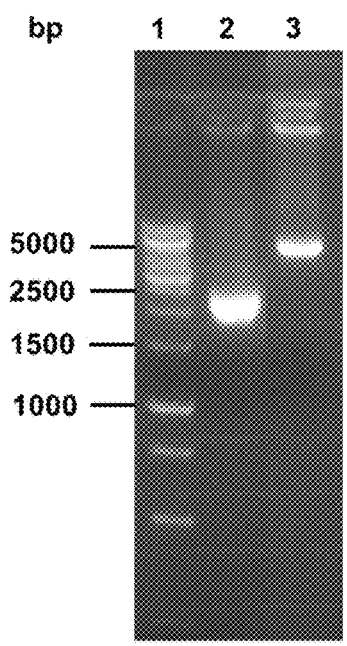
Figure 4B:
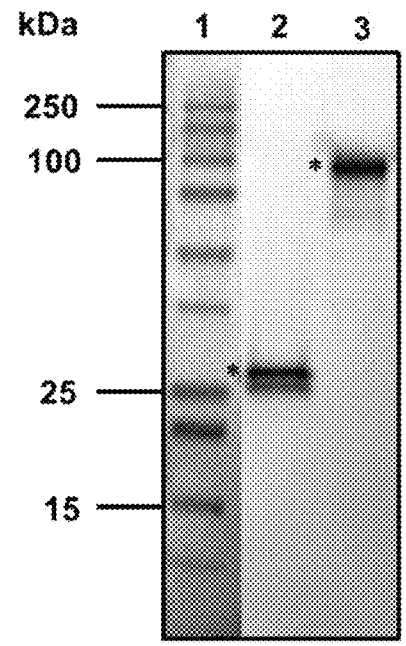
Figure 5:
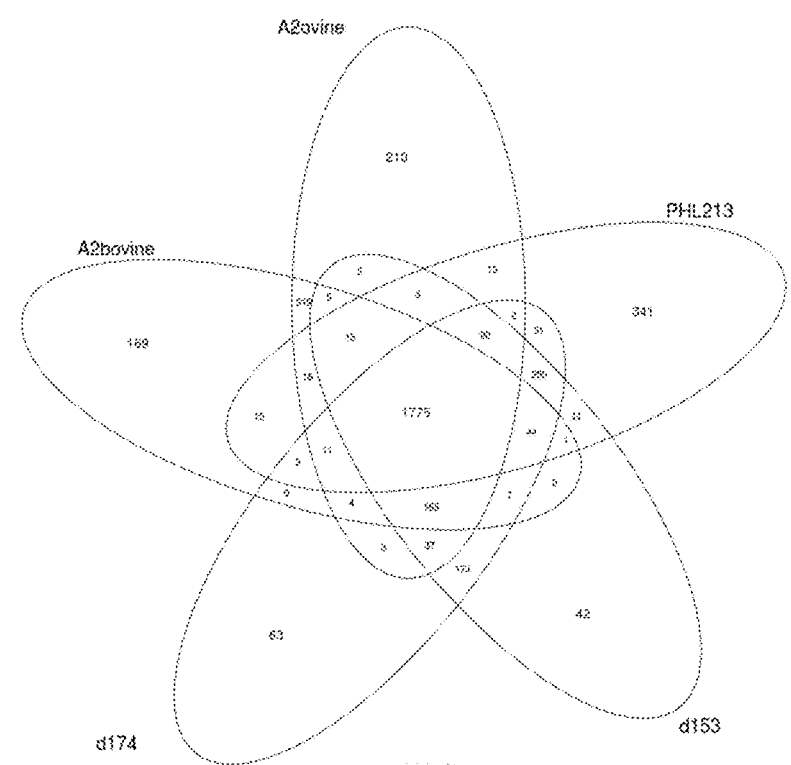

Non-hemolytic mutants were grown in Columbia broth at 37° C. for 3 hours and harvested in late logarithmic growth. Supernatants were dotted onto nitrocellulose along with supernatants from the wild-type parent and a leukotoxin-negative isogenic mutant. After appropriate blocking and washing, the blot was probed with monoclonal anti-leukotoxin antibody 2C9-1E8 (neutralizing antibody produced by NADC, Ames, Iowa). Mutant products containing the native ribosome binding site were found to express low levels of protein reactive to monoclonal antibody, less than that produced by the wild-type parent strain. Products which contained the new ribosome binding site produced much higher levels of reactive protein. Supernatants of two products expressing high levels of leukotoxin were concentrated 15-fold on a 10,000 MW filter (Centriprep, Amicon). The concentrates (1.5 μl) were subjected to SDS-PAGE, blotted to nitrocellulose, and probed with antibody 2C9-1E8. Western blot analysis indicated a new protein reactive with neutralizing anti-leukotoxin monoclonal antibody at an apparent molecular weight consistent with the 27 kDa predicted protein (truncated LktA) product. These representative mutants and single-crossover controls were analyzed by PCR to demonstrate the absence of temperature-sensitive origin and kanamycin-resistance cassette (Step G). The mutant *M. haemolytica* serotype A1 was designated as D153ΔlktCA4-707, which refers to the amino acid positions in LktC and LktA respectively where the deleted region begins and ends. Gene insertion was characterized by PCR amplification using LktCAf (SEQ ID NO:1) and LktCAr (SEQ ID NO:2) primers, which flank the deletion site. As indicated by the gel image, PCR amplification yielded the expected ~2.3 kb for truncated LktCA, and ~5.0 kb for the wildtype bacterium (FIG. 4A). Finally, PCR performed with primers (SEQ ID NOs:1 & 2) flanking is ori and kanamycin resistance genes confirmed those elements were no longer present in the final LktCA mutant for Master Seed (MS). Five microliters of the concentrated culture supernatant was run on a SDS-PAGE system, blotted onto PVDF membrane and probed using mouse anti-LktA, neutralizing antibody 2C9-1E8 (1:1000) as primary antibody. Goat anti-mouse IgG (1:4000) coupled with alkaline phosphatase was used as secondary antibody and developed in a substrate solution containing NBT/BCIP for 1-5 min (FIG. 4B). The lack of functional acylase prevents the activation of LktA, and furthermore, the N-terminal deletion of LktA prevents it from forming pores on host animal neutrophils or macrophages.

Example 2

Efficacy of Attenuated *M. Haemolytica* in Calves

Calves were randomly assigned to one of three groups, each receiving either $10^6$ or $10^7$ CFU of the MH A1+A6 vaccine, or the control RPMI (diluent). Lyophilized *Mannheimia haemolytica* (MH) serotypes A1 and A6 were resuspended and administered intranasally, 1 mL to each nostril, of nine calves, aged 5-6 weeks. The calves were observed for feed intake and rectal temperatures taken morning and evening for 3 days post vaccination. Nasal colonization of *M. haemolytica* A1 and A6 following vaccination was analyzed by RT-QPCR (differentiated among *M. haemolytica* A1 and A6 throughout the study). Vaccines were plated on TSA for exact CFU/ml count on each vaccine the following day.

Challenge. A fresh glycerol stock of virulent MH A1 was grown O/N in BHI medium, plated (TSA) the next day and incubated at 37° C. The following day, plates were scraped and diluted into RPMI medium supplemented with 2% inactivated fetal bovine serum. The inoculum was grown at 37° C./200 rpm until desired $OD_{600}$ was achieved, and the culture was diluted to the desired CFU/challenge dose and dilution plated to enumerate the exact CFU/ml the following day. The remaining inoculum was immediately dilution plated in the lab. Calves were challenged on DAY via trans-tracheal administration of $2.4 \times 10^9$ CFU in 20 ml RPMI, chased with 60 ml RPMI. The calves were monitored for change in behavior including lethargy, coughing, nasal discharge and scored as shown in Table 3. Rectal temperatures were monitored for calves showing clinical signs. The lungs were scored for pneumonic lesions and recorded as % lesion on each lobe, and lung tissue was also collected for histopathology. Swabs were taken from lung lesions and trachea to recover the challenge organism. Table 1 presents the study schedule.

TABLE 1

Study schedule

| Age | Day | Event |
| --- | --- | --- |
| 5-6 weeks old | 0 | Day 0-Bleed, Swab and vaccinate intra-nasally |
| | 7 | 7 days post vax-Bleed and swab |
| | 14 | 14 days post vax-Bleed and swab |
| | 21 | 21 days post vax-Bleed and swab |
| | 22 | 22 days post vax-Bleed, swab & Challenge with *M. haemolytica* A1 |
| | 22-29 | Observe clinical signs starting 8/7, euthanize any calves if necessary. Euthanize and necropsy all on 8/13 |

*Calves were observed for feed intake and rectal temperatures (morning/evening) for 3 days, post vaccination.

Samples from each calf were tested using whole cell, Lkt ELISA and RT-QPCR.

TABLE 2

Clinical signs criteria

| | |
| --- | --- |
| 0= | Normal |
| 1= | Depression, Anorexia, Cough, Nasal Discharge, Dyspnea |
| 2= | Severely Depressed, Unable to Rise or Walk, Euthanized for Humane Reasons |
| 3= | Dead On Arrival (DOA) |

Results. Three days post challenge one of the control calves showed severe signs of pneumonia and was euthanized (36.92% typical *M. haemolytica* lesions). The remaining 8 calves were euthanized on day 6 and their percent lung involvement is described in Table 3. The results clearly indicate that the vaccine affords protection when administered intranasally. As indicated in table 4 intranasal vaccination of *M. haemolytica* A1/A6 combo significantly reduced (62.0% and 76.7% for 6 log and 7 log group respectively) the lung lesions when compared to sham. Furthermore, histopathological analysis clearly indicated typical necrotizing bronchopneumonia characteristic of *M. haemolytica*.

TABLE 4

| Animal # | Actual vaccine dose A1/A6 CFU/animal | Lung lesion (%) | Average lung lesion (%) | Average % reduction in lung lesion compared to sham |
|---|---|---|---|---|
| 125 | $1.19 \times 10^6/9.2 \times 10^5$ | 24.03* | | |
| 176 | $1.19 \times 10^6/9.2 \times 10^5$ | 0.0 | | |
| 188 | $1.19 \times 10^6/9.2 \times 10^5$ | 6.40 | 10.43 | 62.0 |
| 179 | $1.19 \times 10^7/9.2 \times 10^6$ | 0.87 | | |
| 185 | $1.19 \times 10^7/9.2 \times 10^6$ | 1.837 | | |
| 189 | $1.19 \times 10^7/9.2 \times 10^6$ | 14.91* | 6.48 | 76.7 |
| 122 | Sham | 8.85 | | |
| 177 | Sham | 37.75 | | |
| 182 | Sham | 36.92 | 27.84 | |

*The lesions (gross pathology) were due to typical *Mycoplasma bovis* chronic infection Example 3

Development of RT-QPCR Method for Distinguishing Between A1/A6 Serotypes

The efficacy of intranasal colonization of *M. haemolytica* A1/A6 was followed during the course of experiment by a novel QPCR method. Briefly, the genomes of above-described A1 and A6 serotype bacteria were compared against one A1 and two A2 genomes available in GenBank. The comparison revealed 63 genes specific for A1 (D153) and 42 genes specific for A6 (D174). Out of these 105 genes we picked a S6 family IgA-specific metalloendopeptidase (SEQ ID NO:14) specific for A1 and BCCT family betaine/carnitine/choline transporter gene (SEQ ID NO:12) specific for A6 respectively for differential real time PCR. These gene sequences were amplified by using gene specific primers, sequenced by standard Sanger method and verified. Next, we designed real time PCR primers and tagged the probes with two different dyes (A1-5'6 FAM/ZEN/3 and A6-5'Cy5/3'IBRQ) within each gene. To verify the efficacy our assay method we picked *M. haemolytica* colonies from nasal swabs obtained from calves maintained in our facilities 7 days post vaccination. The individual colonies were amplified by multiplex real time colony PCR using QuantiTect Probe PCR kit mastermix (Qiagen) following the manufacturer's instruction in a MX3000P qPCR machine (Stratagene). A1 and A6 colonies verified by serotyping were used as positive controls for multiplex real time quantitative PCR (RT-QPCR). The ct values were set at machine default setting and each colony verified by multiplex real time PCR was confirmed by leukotoxin (LktA) specific PCR. The RT-QPCR results 7 days post vaccination indicated a preferential colonization of A1 over A6 (Table 5), which was further confirmed by leukotoxin gene specific deletion PCR (Table 6). But 14 and 21 days post vaccination indicated essentially exclusive colonization of A1 (Tables 7 & 8).

TABLE 5

RT-QPCR results for nasal swabs from D7 Post Vaccination

| ID | A1 | A6 | ΔLkt |
|---|---|---|---|
| 151-1 | 17 | 11 | + |
| 151-2 | 15 | — | + |
| 151-3 | 16 | — | + |
| 151-4 | 17 | — | + |
| 151-5 | 15 | — | + |
| 154-1 | — | — | |
| 154-2 | — | 39 | |
| 154-3 | — | — | |
| 154-4 | — | — | |
| 154-5 | — | 22 | |
| 157-1 | 15 | — | + |
| 157-2 | 22 | — | + |
| 157-3 | 17 | — | + |
| 157-4 | 15 | 33 | + |
| 157-5 | 16 | — | + |
| 160-1 | 18 | 13 | + |
| 160-2 | — | 12 | + |
| 160-3 | — | 12 | + |
| 160-4 | — | 12 | + |
| 160-5 | — | 11 | + |
| 178-1 | — | — | |
| 178-2 | — | — | |
| 178-3 | — | — | |
| 178-4 | — | 24 | |
| 178-5 | — | 31 | |
| 181-1 | 15 | 15 | + |
| 181-2 | 17 | — | + |
| 181-3 | — | 13 | + |
| 181-4 | 17 | — | + |
| 181-5 | 15 | — | + |
| 183-1 | 16 | 12 | + |
| 183-2 | — | 35 | |
| 183-3 | 17 | — | + |
| 183-4 | 16 | — | + |
| 183-5 | — | 17 | + |
| 186-1 | — | 42 | |
| 186-2 | — | 43 | |
| 186-3 | — | — | |
| 186-4 | — | — | |
| 186-5 | — | 20 | |
| 190-1 | — | — | |
| 190-2 | — | — | |
| 190-3 | — | 10 | |
| 190-4 | — | — | |
| 190-5 | — | — | |
| 193-1 | 15 | 38 | + |
| 193-2 | 15 | — | + |
| 193-3 | — | 36 | |
| 193-4 | 16 | 20 | + |
| 193-5 | — | — | |
| A1 mut. Vx | 15 | — | + |
| A6 mut. Vx | — | 11 | + |
| Neg | — | – | |

TABLE 6

PCR results for nasal swabs from D7 Post Vaccination

| ID/colony | A1 | A6 | Lkt Δ | ~2300 bp |
|---|---|---|---|---|
| 122-1 | — | — | | |
| 122-2 | — | — | | |
| 122-3 | — | — | | |
| 122-4 | — | — | | |
| 122-5 | — | — | | |
| 125-1 | 16 | — | + | Y |
| 125-2 | 17 | — | + | Y |
| 125-3 | 17 | — | + | Y |
| 125-4 | 16 | — | + | Y |
| 125-5 | 17 | — | + | Y |
| 176-1 | 17 | — | + | Y |
| 176-2 | 17 | — | + | Y |
| 176-3 | 16 | — | + | Y |

TABLE 6-continued

PCR results for nasal swabs from D7 Post Vaccination

| ID/colony | A1 | A6 | Lkt Δ | ~2300 bp |
|---|---|---|---|---|
| 176-4 | 16 | — | + | Y |
| 176-5 | 16 | — | + | Y |
| 177-1 | — | — | | |
| 177-2 | — | — | | |
| 177-3 | — | — | | |
| 177-4 | — | — | | |
| 177-5 | — | — | | |
| 179-1 | 17 | — | + | Y |
| 179-2 | 16 | — | + | Y |
| 179-3 | — | — | | |
| 179-4 | 16 | — | + | Y |
| 179-5 | 29 | — | + | Y |
| 182-1 | — | — | | |
| 182-2 | — | — | | |
| 182-3 | — | — | | |
| 182-4 | — | — | | |
| 182-5 | — | — | | |
| 185-1 | — | 15 | + | Y |
| 185-2 | 18 | — | + | Y |
| 185-3 | 16 | — | + | Y |
| 185-4 | — | — | + | Y |
| 185-5 | 22 | — | + | Y |
| 188-1 | — | — | | |
| 188-2 | — | — | | |
| 188-3 | — | — | | |
| 188-4 | — | — | | |
| 188-5 | — | — | | |
| 189-1 | 16 | — | + | Y |
| 189-2 | 16 | — | + | Y |
| 189-3 | 21 | — | + | Y |
| 189-4 | 16 | — | + | Y |
| 189-5 | 17 | — | + | |
| Neg | — | — | | |

TABLE 7

PCR results for nasal swabs from D14 Post Vaccination

| ID-colony # | A1 | A6 | Lkt Δ PCR | Lkt Δ |
|---|---|---|---|---|
| 122-1 (Con. | 0 | 0 | Neg | |
| 122-2 (Con. | 0 | 0 | Neg | |
| 122-3 (Con. | 0 | 0 | Neg | |
| 125-1 (6 log) | 15 | 0 | Pos | Y |
| 125-2 (6 log) | 16 | 0 | Pos | Y |
| 125-3 (6 log) | 16 | 0 | Pos | Y |
| 176-1 (6 log) | 0 | 0 | Neg | |
| 176-2 (6 log) | 0 | 0 | Neg | |
| 176-3 (6 log) | 0 | 0 | Neg | |
| 177-1 (Con. | 0 | 0 | Neg | |
| 177-2 (Con. | 0 | 0 | Neg | |
| 177-3 (Con. | 0 | 0 | Neg | |
| 179-1 (7 log) | 0 | 0 | Neg | |
| 179-2 (7 log) | 0 | 0 | Neg | |
| 179-3 (7 log) | 0 | 0 | Neg | |
| 182-1 (Con.) | 0 | 0 | Neg | |
| 182-2 (Con.) | 0 | 0 | Neg | |
| 182-3 (Con.) | 0 | 0 | Neg | |
| 185-1 (7 log) | 0 | 0 | Neg | |
| 185-2 (7 log) | 0 | 0 | Neg | |
| 185-3 (7 log) | 0 | 0 | Neg | |
| 188-1 (6 log) | 0 | 0 | Neg | |
| 188-2 (6 log) | 0 | 0 | Neg | |
| 188-3 (6 log) | 0 | 0 | Neg | |
| 189-1 (7 log) | 15 | 0 | Pos | Y |
| 189-2 (7 log) | 15 | 0 | Pos | Y |
| 189-3 (7 log) | 15 | 0 | Pos | Y |
| A1 Mutant Pos | 15 | 0 | Pos | Y |
| A6 Mutant Pos | 0 | 16 | Pos | Y |
| Neg Con. | 0 | 0 | Neg | |

TABLE 8

PCR results for nasal swabs from D21 Post Vaccination

| ID-colony # | A1 | A6 | Lkt Δ PCR | Lkt Δ |
|---|---|---|---|---|
| 122-1 (Con.) | 0 | 0 | | Δ |
| 122-2 (Con.) | 0 | 0 | | |
| 122-3 (Con.) | 0 | 0 | | |
| 125-1 (6 log) | 14 | 0 | + | Y |
| 125-2 (6 log) | 15 | 0 | + | Y |
| 125-3 (6 log) | 15 | 0 | + | Y |
| 176-1 (6 log) | 15 | 0 | + | Y |
| 176-2 (6 log) | 15 | 0 | + | Y |
| 176-3 (6 log) | 15 | 0 | + | Y |
| 177-1 (Con.) | 0 | 0 | | |
| 177-2 (Con.) | 0 | 0 | | |
| 177-3 (Con.) | 0 | 0 | | |
| 179-1 (7 log) | 0 | 0 | | |
| 179-2 (7 log) | 0 | 0 | | |
| 179-3 (7 log) | 0 | 0 | | |
| 182-1 (Con.) | 0 | 0 | | |
| 182-2 (Con.) | 0 | 0 | | |
| 182-3 (Con.) | 0 | 0 | | |
| 185-1 (7 log) | 15 | 0 | + | |
| 185-2 (7 log) | 14 | 0 | + | Y |
| 185-3 (7 log) | 15 | 0 | + | Y |
| 188-1 (6 log) | 14 | 0 | + | Y |
| 188-2 (6 log) | 15 | 0 | + | Y |
| 188-3 (6 log) | 14 | 0 | + | Y |
| 189-1 (7 log) | 16 | 0 | + | Y |
| 189-2 (7 log) | 17 | 0 | + | Y |
| 189-3 (7 log) | 15 | 0 | + | Y |
| A1 Mutant Pos | 15 | 0 | + | Y |
| A6 Mutant Pos | 0 | 16 | + | Y |
| Neg Control | 0 | 0 | neg | |
| Pre Challenge A1 Wt | 15 | 0 | + | WT |
| Post Challenge A1 Wt | 16 | 0 | + | WT |

Example 3

Intranasal Vaccination of Calves Using *Mannheimia haemolytica* A1 & A6 Vaccines Followed by Virulent Challenge Fifteen calves, 4 weeks of age and housed in 3 different pens/5 calves per pen, were randomly assigned to one of the two treatment groups. Calves were vaccinated intranasally with modified live. *Mannheimia haemolytica* serotypes A1 and A6 (reconstituted from lyophilized, Table 9), and intranasal colonization of A1 and A6 was monitored by real time PCR. Calves were finally challenged with virulent *M. haemolytica* A6 (wild type) to determine vaccine efficacy.

TABLE 9

Treatment Groups.

| Group | Treatment | Total Dose/CFU per animal | Route/volume | Calf Id # |
|---|---|---|---|---|
| 1 | *M. haemolytica* A1 + A6 | $10^7$ (1.43 × $10^6$ + 8.63 × $10^5$)* | Intranasal 1 ml per nostril | 2, 4, 6 8, 10 |
| 2 | *M. haemolytica* A1 + A6 | $10^8$ (1.43 × $10^7$ + 8.63 × $10^6$)* | Intranasal 1 ml per nostril | 1, 3, 5, 7, 9 |
| 3 | Control-Lyophilized RPMI + stabilizer | control | Intranasal 1 ml per nostril | 162, 166, 170, 174, 175 |

*Actual CFU/ml based on plate count

Vaccination. Lyophilized cultures of *M. haemolytica* A1 and A6 were enumerated from a batch stored at 4° C. On vaccination day, the vaccines were diluted in RPMI (colorless) to required CFU/ml for each isolate. Similarly, the sham vaccine (lyophilized RPMI in stabilizer) was diluted in RPMI. The vaccines were plated on TSA to determine the exact CFU/ml count on each vaccine the following day. The vaccines were mixed and administered 1 ml/nostril using a repeat syringe attached with a cannula according to the dose in Table 9. The control group was vaccinated first, followed by the lowest to highest log group. Following vaccination, the samples were collected as described in Table 10, and the calves were observed for feed intake and rectal temperatures taken morning and evening for 3 days post vaccination. Nasal colonization of M. haemolytica A1 and A6 following vaccination was analyzed by Q-PCR as described above.

M. haemolytica A6 challenge culture. A fresh glycerol stock of M. haemolytica A6 was grown O/N in BHI medium, plated (TSA) the next day and incubated at 37° C. The following day, plates were scraped and diluted into RPMI medium supplemented with 2% inactivated fetal bovine serum. The inoculum was grown at 37° C./200 rpm until desired $OD_{600}$ was achieved. The culture was diluted to desired CFU/challenge dose and dilution plated to enumerate the exact CFU/ml the following day. The inoculum was transported on ice and kept on ice during challenge, and administered trans-tracheally using a 14G×1 inch needle. The dose was $1.09 \times 10^9$ CFU/animal in 20 ml RPMI, chased with 60 ml RPMI. Once completed, the remaining inoculum was immediately dilution plated. The calves were monitored for behavior changes including lethargy, coughing, and nasal discharge and scored as shown in Table 11. Rectal temperatures were monitored for calves showing clinical signs. The lungs were scored for pneumonic lesions and recorded as % lesion on each lobe, and tissues were collected for histopathology. Swabs were also taken from lungs (lesions) and trachea to recover the challenge organism.

TABLE 10

Study Schedule.

| Age | Date | Event |
| --- | --- | --- |
| 4 weeks old | 0 | Day 0-Bleed, Swab and vaccinate intra-nasally |
| | 7 days post vax | 7 days post vax-Bleed and swab |
| | 15 days post vax | 15 days post vax-Bleed and swab & Challenge with M. haemolytica A6 |
| | 15 to 20 days post vax | Observe clinical signs starting day 15; euthanized any calves when necessary. Euthanized and necropsy all on day 20 |

* Feed intake (daily) and rectal temperatures (twice daily) were monitored for 3 days post vaccination.

TABLE 11

Clinical signs.
Criteria for Post Challenge Observations

| | |
| --- | --- |
| 0= | Normal |
| 1= | Depression, Anorexia, Cough, Nasal Discharge, Dyspnea |
| 2= | Severely Depressed, Unable to Rise or Walk, Euthanized for Humane Reasons |
| 3= | Dead On Arrival (DOA) |

Results. Two days post challenge calf# 5 and 174 showed severe signs of pneumonia and were euthanized. Calf #7 died on day 3, post challenge. The remaining 12 calves were euthanized on day 5 and their % lung involvement is described in Table 4. The results indicate that 80% of vaccinates were protected by the modified live M. haemolytica A1/A6 vaccine. From the 7 log group, three (1, 3 and 9) animals were protected while the other two animals (5, 7) had significantly large lesions compared to controls. The large lesions could have been caused by an existing Mannheimia, mycoplasma or viral infection, which had been exacerbated by challenge. Overall, 80% of vaccinates (1, 2, 3, 4, 6, 8, 9 and 10) had significantly (89.55% reduction) reduced lung lesion as compared to control, and histopathological analysis indicated typical necrotizing bronchopneumonia in the control animals.

TABLE 12

Dosage groups.

| Group | Animal # | Actual A1/A6 vaccine dose CFU/animal | Lung lesion (%) | Average lung lesion (%) | Average % reduction in lung lesion compared to sham vaccine |
| --- | --- | --- | --- | --- | --- |
| $10^7$ | 2 | $1.43 \times 10^6 / 8.63 \times 10^5$ | 0.0 | | |
| | 4 | $1.43 \times 10^6 / 8.63 \times 10^5$ | 8.67 | | |
| | 6 | $1.43 \times 10^6 / 8.63 \times 10^5$ | 5.92 | | |
| | 8 | $1.43 \times 10^6 / 8.63 \times 10^5$ | 4.83 | | |
| | 10 | $1.43 \times 10^6 / 8.63 \times 10^5$ | 0.0 | 3.88 | 85.04 |
| $10^8$ | 1 | $1.43 \times 10^7 / 8.63 \times 10^6$ | 0.0 | | |
| | 3 | $1.43 \times 10^7 / 8.63 \times 10^6$ | 0.0 | | |
| | 5 | $1.43 \times 10^7 / 8.63 \times 10^6$ | 41.58 | | |
| | 7 | $1.43 \times 10^7 / 8.63 \times 10^6$ | 64.47 | | |
| | 9 | $1.43 \times 10^7 / 8.63 \times 10^6$ | 2.295 | 21.66 | 14.47 |
| | 162 | Sham | 37.11 | | |
| | 166 | Sham | 29.82 | | |
| | 170 | Sham | 11.235 | | |
| | 174 | Sham | 25.54 | | |
| | 175 | Sham | 25.97 | 25.93 | |

The efficacy of intranasal colonization of M. haemolytica A1/A6 was followed during the course of experiment by above-described QPCR methods. Results for 7 and 15 days post-vaccination indicated vaccinates had a preferential colonization of A1 over A6 which was further confirmed by leukotoxin gene specific deletion PCR (Tables 13 & 14).

TABLE 13

Day 7 Post Vaccination

| Sample # | Animal # | FAM MH A1 | MH A1? | CY5 MHA6 | MH A6? |
| --- | --- | --- | --- | --- | --- |
| 1 | 1 | No Ct | | 16.5 | + |
| 2 | 1 | No Ct | | 38.26 | + |
| 3 | 1 | No Ct | | 16.53 | + |
| 4 | 1 | No Ct | | 25 | + |
| 5 | 2 | No Ct | | No Ct | |
| 6 | 2 | No Ct | | No Ct | |
| 7 | 2 | No Ct | | No Ct | |
| 8 | 2 | 17.01 | + | No Ct | |
| 9 | 3 | No Ct | | 15.87 | + |
| 10 | 3 | 25.11 | + | 20.81 | + |
| 11 | 3 | 21.91 | + | 19.69 | + |
| 12 | 3 | 22.35 | + | 21.8 | + |
| 13 | 4 | 16.52 | + | No Ct | |
| 14 | 4 | 17.11 | + | No Ct | |
| 15 | 4 | 16.26 | + | No Ct | |
| 16 | 4 | 16 | + | No Ct | |
| 17 | 5 | 39.07 | + | 41.17*Plot was bad ~ NEG | |
| 18 | 5 | 15.98 | + | No Ct | |
| 19 | 5 | 16.4 | + | No Ct | |
| 20 | 5 | 16.44 | + | No Ct | |
| 21 | 6 | 17.08 | + | No Ct | |
| 22 | 6 | 18.24 | + | No Ct | |
| 23 | 6 | 16.8 | + | No Ct | |
| 24 | 6 | 17.94 | + | No Ct | |

TABLE 13-continued

Day 7 Post Vaccination

| Sample # | Animal # | FAM MH A1 | MH A1? | CY5 MHA6 | MH A6? |
|---|---|---|---|---|---|
| 25 | 7 | 17.98 | + | No Ct | |
| 26 | 7 | No Ct | | 16.34 | + |
| 27 | 7 | 26.57 | + | 15.46 | + |
| 28 | 7 | 16.7 | + | 17.52 | + |
| 29 | 8 | 16.7 | + | No Ct | |
| 30 | 8 | 16.71 | + | No Ct | |
| 31 | 8 | 16.1 | + | No Ct | |
| 32 | 8 | 15.16 | + | No Ct | |
| 33 | 9 | 16.32 | + | No Ct | |
| 34 | 9 | 17.03 | + | No Ct | |
| 35 | 9 | 16.63 | + | No Ct | |
| 36 | 9 | 16.04 | + | No Ct | |
| 37 | 10 | No Ct | | No Ct | |
| 38 | 10 | No Ct | | No Ct | |
| 39 | 10 | No Ct | | No Ct | |
| 40 | 10 | No Ct | | No Ct | |
| 41 | 162 | No Ct | | No Ct | |
| 42 | 162 | No Ct | | No Ct | |
| 43 | 162 | No Ct | | No Ct | |
| 44 | 162 | No Ct | | No Ct | |
| 45 | 166 | No Ct | | No Ct | |
| 46 | 166 | No Ct | | No Ct | |
| 47 | 166 | No Ct | | No Ct | |
| 48 | 166 | No Ct | | No Ct | |
| 49 | 170 | No Ct | | No Ct | |
| 50 | 170 | No Ct | | No Ct | |
| 51 | 170 | No Ct | | No Ct | |
| 52 | 170 | No Ct | | No Ct | |
| 53 | 174 | No Ct | | No Ct | |
| 54 | 174 | No Ct | | No Ct | |
| 55 | 174 | No Ct | | No Ct | |
| 56 | 174 | No Ct | | No Ct | |
| 57 | 175 | No Ct | | No Ct | |
| 58 | 175 | No Ct | | No Ct | |
| 59 | 175 | No Ct | | No Ct | |
| 60 | 175 | No Ct | | No Ct | |
| 61 | A1 mut + | 16.66 | | No Ct | |
| 62 | A6 mut + | No Ct | | 13.85 | |
| 63 | A1 Wt + | 15.87 | | No Ct | |
| 64 | Neg | 40.77 | | No Ct | |

TABLE 14

Day 15 Post Vaccination

| Animal # | FAM MHA1 | MHA1? | CY5 MHA6 | MHA6? | Lkt del PCR |
|---|---|---|---|---|---|
| 1 | No Ct | | 40.53 | | |
| 1 | No Ct | | No Ct | | |
| 1 | No Ct | | No Ct | | |
| 1 | No Ct | | No Ct | | |
| 1 | No Ct | | No Ct | | |
| 2 | No Ct | | No Ct | | |
| 2 | No Ct | | No Ct | | |
| 2 | No Ct | | No Ct | | |
| 2 | No Ct | | No Ct | | |
| 2 | No Ct | | No Ct | | |
| 3 | No Ct | | 15.1 | + | Mutant |
| 3 | No Ct | | 15.08 | + | Mutant |
| 3 | No Ct | | 15.19 | + | Mutant |
| 3 | No Ct | | 15.3 | + | Mutant |
| 3 | No Ct | | 15.1 | + | Mutant |
| 4 | 15.82 | | No Ct | | Mutant |
| 4 | No Ct | | No Ct | | |
| 4 | No Ct | | No Ct | | |
| 4 | No Ct | | No Ct | | |
| 4 | No Ct | | No Ct | | |
| 5 | 16.13 | + | No Ct | | Mutant |
| 5 | 15.27 | + | No Ct | | Mutant |
| 5 | 17.03 | + | No Ct | | Mutant |
| 5 | 16.49 | + | No Ct | | Mutant |
| 5 | 18.06 | + | No Ct | | Mutant |
| 6 | No Ct | | No Ct | | |
| 6 | No Ct | | No Ct | | |
| 6 | 40.05 | | No Ct | | |
| 6 | No Ct | | No Ct | | |
| 7 | No Ct | | 16.83 | + | Mutant |
| 7 | No Ct | | No Ct | + | |
| 7 | No Ct | | 14.92 | + | Mutant |
| 7 | No Ct | | 15.21 | + | Mutant |
| 7 | No Ct | | 16.16 | + | Mutant |
| 8 | No Ct | | No Ct | | |
| 8 | No Ct | | No Ct | | |
| 8 | No Ct | | No Ct | | |
| 8 | No Ct | | No Ct | | |
| 9 | No Ct | | No Ct | | |
| 9 | No Ct | | No Ct | | |
| 9 | No Ct | | No Ct | | |
| 9 | No Ct | | No Ct | | |
| 10 | 15.94 | + | No Ct | | Mutant |
| 10 | No Ct | + | No Ct | | |
| 10 | No Ct | + | No Ct | | |
| 10 | 23.82 | + | No Ct | | Mutant |
| 10 | 30.04 | + | No Ct | | Mutant |
| 162 | No Ct | | No Ct | | |
| 162 | No Ct | | No Ct | | |
| 162 | No Ct | | No Ct | | |
| 162 | No Ct | | No Ct | | |
| 162 | No Ct | | No Ct | | |
| 166 | No Ct | | No Ct | | |
| 166 | No Ct | | No Ct | | |
| 166 | No Ct | | No Ct | | |
| 166 | No Ct | | No Ct | | |
| 166 | No Ct | | No Ct | | |
| 170 | No Ct | | No Ct | | |
| 170 | No Ct | | No Ct | | |
| 170 | No Ct | | No Ct | | |
| 170 | No Ct | | No Ct | | |
| 170 | No Ct | | No Ct | | |
| 174 | No Ct | | No Ct | | |
| 174 | No Ct | | No Ct | | |
| 174 | No Ct | | No Ct | | |
| 174 | No Ct | | No Ct | | |
| 174 | No Ct | | No Ct | | |
| 175 | 16.24 | + | No Ct | | Mutant |
| 175 | No Ct | + | No Ct | | |
| 175 | 16.54 | + | No Ct | | Mutant |
| 175 | No Ct | + | No Ct | | Mutant |
| 175 | 23.06 | + | No Ct | | Mutant |

\* \* \*

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. A non-adjuvanted, intranasal vaccine comprising an attenuated *Mannheimia haemolytica* (*M haemolytica*) A1 strain and an attenuated *M haemolytica* A6 strain, which vaccine provides a safe and protective immune response in a bovine animal against both *M. haemolytica* strains A1 and A6, or diseases caused by *M. haemolytica* strains A1 and A6.

2. The vaccine of claim 1, wherein both the A1 and A6 strains contain nucleic acid deletions in their respective leukotoxin A (lktA) genes, which deletions have rendered the strains attenuated relative to the virulent parental strains A1 and A6 from which the attenuated strains A1 and A6 were produced.

3. The vaccine of claim 1, consisting essentially of the attenuated A1 and A6 strains.

4. The vaccine of claim 1, further comprising an additional antigen, which is capable of eliciting a safe and effective response in said bovine against a bovine disease or pathogen other than *M haemolytica*.

5. The vaccine of claim 1, wherein a safe and protective intranasal dose of the vaccine comprises from about $1.19 \times 10^6$ to $1.19 \times 10^7$ CFU of the attenuated A1 strain and from about $9.2 \times 10^5$ to $9.2 \times 10^6$ CFU of the attenuated A6 strain.

6. The vaccine of claim 1, further comprising a pharmaceutically or veterinary acceptable vehicle, diluent or excipient and from about $1.19 \times 10^6$ to $1.19 \times 10^7$ CFU of the attenuated A1 strain and from about $9.2 \times 10^5$ to $9.2 \times 10^6$ CFU of the attenuated A6 strain.

7. The vaccine of claim 1, provided in lyophilized form.

8. The vaccine of claim 1, which provides the protective immune response in the bovine against an experimental challenge of about $1.09 \times 10^9$ CFU of virulent *M. haemolytica* strain A6.

9. The vaccine of claim 1, which provides the protective immune response in the bovine against an experimental challenge of about $2.4 \times 10^9$ CFU of virulent *M. haemolytica* strain A1.

10. The vaccine of claim 1, further comprising at least two additional antigens associated with a bovine pathogen other than *M haemolytica*.

11. A method of vaccinating an animal comprising administering at least one dose of the vaccine of claim 1.

12. The method of claim 11, wherein the animal is a bovine.

13. The method of claim 12, wherein the bovine is a calf that is 28 days or older.

14. The method of claim 13, wherein the vaccine is administered in about equal portions to both of the anima's nostrils.

15. An immunological composition suitable for the prevention of bovine respiratory disease caused by *M haemolytica*, comprising the vaccine of claim 1, and further comprising an immunologically effective amount of an attenuated *Pasteurella multocida* (*P. multocida*) strain and an attenuated *Histophilus somni* (*H. somni*) strain.

16. The composition of claim 15, comprising from about $1.19 \times 10^6$ CFU to about $1.19 \times 10^7$ CFU of the attenuated A1 strain and from about $9.2 \times 10^5$ CFU to about $9.2 \times 10^6$ CFU of the attenuated A6 strain.

17. The composition of claim 15, consisting essentially of the attenuated *M haemolytica* A1 and A6 strains, the attenuated *P. multocida* strain and the attenuated *H. somni* strain.

18. The composition of claim 17, provided in lyophilized form inside of a sterile vial.

19. A kit for preventing bovine respiratory disease comprising effective amounts of an immunological composition, comprising a non-adjuvanted, intranasal vaccine comprising an attenuated *M. haemolytica* A1 strain and an attenuated *M. haemolytica* A6 strain, wherein the vaccine provides a safe and protective immune response in a bovine animal against both *M. haemolytica* strains A1 and A6, or diseases caused by *M. haemolytica* strains A1 and A6, wherein the kit further comprising an immunologically effective amount of an attenuated *P. multocida* strain and an attenuated *H. somni* strain, provided in lyophilized form, and, a diluent for resuspending the lyophilized, attenuated strains.

\* \* \* \* \*